US011780907B2

United States Patent
Purcell et al.

(10) Patent No.: US 11,780,907 B2
(45) Date of Patent: *Oct. 10, 2023

(54) HUMAN ANTIBODIES TO INFLUENZA HEMAGGLUTININ

(71) Applicant: Regeneron Pharmaceuticals, Inc., Tarrytown, NY (US)

(72) Inventors: Lisa A. Purcell, Yorktown Heights, NY (US); Jonathan Viau, White Plains, NY (US); William Olson, Yorktown Heights, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 404 days.

This patent is subject to a terminal disclaimer.

(21) Appl. No.: 16/964,579

(22) PCT Filed: Jan. 24, 2019

(86) PCT No.: PCT/US2019/015029
§ 371 (c)(1),
(2) Date: Jul. 23, 2020

(87) PCT Pub. No.: WO2019/147867
PCT Pub. Date: Aug. 1, 2019

(65) Prior Publication Data
US 2021/0371505 A1  Dec. 2, 2021

Related U.S. Application Data

(60) Provisional application No. 62/622,480, filed on Jan. 26, 2018.

(51) Int. Cl.
| *C07K 16/10* | (2006.01) |
| *A61P 31/16* | (2006.01) |
| *A61K 31/215* | (2006.01) |
| *A61K 39/42* | (2006.01) |
| *A61K 39/00* | (2006.01) |

(52) U.S. Cl.
CPC ........ *C07K 16/1018* (2013.01); *A61K 31/215* (2013.01); *A61K 39/42* (2013.01); *A61P 31/16* (2018.01); *A61K 2039/505* (2013.01); *C07K 2317/21* (2013.01); *C07K 2317/732* (2013.01); *C07K 2317/734* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 6,180,370 B1 * | 1/2001 | Queen ............... A61P 31/12 435/69.6 |
| 6,596,541 B2 | 7/2003 | Murphy et al. |
| 7,582,298 B2 | 9/2009 | Stevens et al. |
| 8,246,995 B2 | 8/2012 | Dai et al. |
| 8,257,740 B1 | 9/2012 | Sung et al. |
| 8,383,121 B2 | 2/2013 | Ho et al. |
| 8,444,986 B2 | 5/2013 | Qian et al. |
| 8,470,327 B2 | 6/2013 | Throsby et al. |
| 8,540,995 B2 | 9/2013 | Mookkan et al. |
| 8,540,996 B2 | 9/2013 | Qian et al. |
| 8,574,581 B2 | 11/2013 | Qian et al. |
| 8,574,830 B2 | 11/2013 | Mookkan et al. |
| 8,637,644 B2 | 1/2014 | Ho et al. |
| 8,637,645 B2 | 1/2014 | Ho et al. |
| 8,685,402 B2 | 4/2014 | Lanzavecchia |
| 8,691,223 B2 | 8/2014 | Van Den Brink et al. |
| 8,871,207 B2 | 10/2014 | Lanzavecchia |
| 9,169,318 B2 | 10/2015 | Horowitz et al. |
| 9,284,365 B2 * | 3/2016 | Xu ............... A61P 43/00 |
| 9,920,094 B2 | 3/2018 | Zhang et al. |

(Continued)

FOREIGN PATENT DOCUMENTS

| EP | 2380976 | 10/2011 |
| EP | 3011968 A1 | 4/2016 |

(Continued)

OTHER PUBLICATIONS

Kipriyanov, Sergey M., and Fabrice Le Gall. "Generation and production of engineered antibodies." Molecular biotechnology 26.1 (2004): 39-60. (Year: 2004).*

Janeway, Charles A. "Immunobiology: The Immune System in Health and Disease." 2001 (Year: 2001).*

Marjuki et al. (2016) "Human Monoclonal Antibody 81.39a Effectively Neutralizes Emerging Influenza A Viruses of Group 1 and 2 Hemagglutinins", J. Virology, 90(23):10446-10458.

(Continued)

Primary Examiner — Michael Szperka
Assistant Examiner — Lia E Taylor
(74) Attorney, Agent, or Firm — FisherBroyles, LLP; Cara L. Crowley-Weber; Gabriele Amodeo

(57) ABSTRACT

The present invention provides monoclonal antibodies, or antigen-binding fragments thereof, that bind to the influenza hemagglutinin (HA) protein, pharmaceutical compositions comprising the antibodies and methods of use. The antibodies of the invention are useful for inhibiting or neutralizing influenza virus activity, thus providing a means of treating or preventing influenza infection in humans. In some embodiments, the invention provides for use of one or more antibodies that bind to the influenza HA for preventing viral attachment and/or entry into host cells. The antibodies of the invention may be used prophylactically or therapeutically and may be used alone or in combination with one or more other anti-viral agents or vaccines.

26 Claims, 10 Drawing Sheets

Specification includes a Sequence Listing.

(56) References Cited

U.S. PATENT DOCUMENTS

| | | |
|---|---|---|
| 10,143,186 B2 | 12/2018 | McWhirter et al. |
| 2004/0101920 A1 | 5/2004 | Radziejewski et al. |
| 2010/0004063 A1 | 1/2010 | Rebmann |
| 2010/0331527 A1 | 12/2010 | Davis et al. |
| 2011/0319600 A1 | 12/2011 | Ikuta et al. |
| 2012/0020971 A1 | 1/2012 | Kauvar et al. |
| 2012/0058124 A1 | 3/2012 | Kurosawa et al. |
| 2012/0128671 A1 | 5/2012 | Horowitz et al. |
| 2012/0276115 A1 | 11/2012 | Van Den Brink et al. |
| 2013/0004505 A1 | 1/2013 | Chang et al. |
| 2013/0243792 A1 | 9/2013 | Vogels et al. |
| 2013/0289246 A1 | 10/2013 | Crowe et al. |
| 2013/0302349 A1 | 11/2013 | Shriver et al. |
| 2014/0011982 A1 | 1/2014 | Marasco et al. |
| 2014/0065156 A1 | 3/2014 | Van Den Brink et al. |
| 2014/0065165 A1 | 3/2014 | Vogels et al. |
| 2014/0120113 A1 | 5/2014 | Kwaks et al. |
| 2014/0161822 A1 | 6/2014 | Xu et al. |
| 2014/0322196 A1 | 10/2014 | Superti et al. |
| 2014/0322210 A1 | 10/2014 | Kauvar et al. |
| 2016/0052997 A1 | 2/2016 | Hong et al. |
| 2016/0176953 A1 | 6/2016 | Purcell et al. |
| 2016/0289304 A1 | 10/2016 | Bucher et al. |

FOREIGN PATENT DOCUMENTS

| | | | |
|---|---|---|---|
| WO | WO 2005/103081 | 11/2005 | |
| WO | WO-2006124784 A2 * | 11/2006 | ......... C12N 15/1034 |
| WO | WO 2008/028946 | 3/2008 | |
| WO | WO 2009/079259 | 6/2009 | |
| WO | WO 2010/010466 | 1/2010 | |
| WO | WO 2010/027818 | 3/2010 | |
| WO | WO 2010/130636 | 11/2010 | |
| WO | WO 2011/111966 | 9/2011 | |
| WO | WO 2012/045001 | 4/2012 | |
| WO | WO 2013/007770 | 1/2013 | |
| WO | WO 2013/081463 | 6/2013 | |
| WO | WO 2013170139 | 11/2013 | |
| WO | WO 2014/158001 | 2/2014 | |
| WO | WO 2014078268 | 5/2014 | |
| WO | WO 2014/121087 | 8/2014 | |
| WO | WO 2015/051010 A1 | 4/2015 | |
| WO | WO 2015/120097 A2 | 8/2015 | |
| WO | WO 2015/148806 | 10/2015 | |
| WO | WO 2016/100807 A2 | 6/2016 | |
| WO | WO-2016100807 A2 * | 6/2016 | ........... A61K 31/215 |
| WO | WO 2016/164835 A1 | 10/2016 | |
| WO | WO 2016/196470 | 12/2016 | |
| WO | WO 2017/192589 A1 | 11/2017 | |
| WO | WO 2020/221908 | 11/2020 | |

OTHER PUBLICATIONS

Tan et al. (2014) "Characterization of a Broadly Neutralizing Monoclonal Antibody That Targets the Fusion Domain of Group 2 Influenza A Virus Hemagglutinin", J. Virology, 88(23):13580-13592.

Krieg et al. (2005) "Funcitional Analysis of B and T Lymphocyte Attenuator Engagement on CD4+ and CD8+ T Cells", Journal of Immunology, 175(10):6420-6427.

An et al. (2009) "IgG2m4, an Engineered Antibody Isotype with Reduced Fc Function", Mabs, 1(6): 572-579.

Bostrom et al. (2009) "Improving Antibody Binding Affinity and Specificity for Therapeutic Development", Methods Mol. Biol., 525:353-376.

Gonzales, et al. (2005) "Minimizing the Immunogenicity of Antibodies for Clinical Application", TumorBiology, 26(1):31-43.

Kunik et al. (2012) "Structural Consensus Among Antibodies Defines the AntigenBinding Site", PLoS Comput Biol., 8(2):e1002388, 12 pages.

Wark and Hudson (2006) "Latest Technologies for the Enhancement of Antibody Affinity", Advanced Drug Delivery Reviews, 58:657-670.

Abdiche et al. (2008) "Determining Kinetics and Affinities of Protein Interactions Using a Parallel Real-Time Label-Free Biosensor, the Octet", Analytical Biochemistry, 377(2):209-217.

Al-Lazikani et al. (1997) "Standard Conformations for the Canonical Structures of Immunoglobulins", J. Mol. Biol., 273:927-948.

Altschul et al. (1990) "Basic Local Alignment Search Tool", J. Mol. Biol., 215: 403-410.

Altschul et al. (1997) "Gapped BLAST and PSI-BLAST: a New Generation of Protein Database Search Programs", Nucleic Acids Res., 25:3389-3402.

Arruebo et al. (2009) "Antibody Conjugated Nanoparticles for Biomedical Applications", J. Nanomat., vol. 2009, Article ID 439389, 24 pages, doi: 10.1155/2009/439389.

Ehring (1999) "Hydrogen Exchange/Electrospray Ionization Mass Spectrometry Studies of Structural Features of Proteins and Protein/Protein Interactions", Analytical Biochemistry, 267: 252-259.

Ekiert, et al. (2011) "A Highly Conserved Neutralizing Epitope on Group 2 Influenza A Viruses", Science 333(6044):843-850.

Engen and Smith (2001) "Peer Reviewed: Investigating Protein Structure and Dynamics by Hydrogen Exchange MS", Anal. Chem., 73: 256A-265A.

Gonnet et al. (1992) "Exhaustive Matching of the Entire Protein Sequence Database", Science, 256: 1443-1445.

Good et al. (1991) "Historic Aspects of Intravenous Immunoglobulin Therapy", Cancer, 68:1415-1421.

International Search Report from PCT/US2019/015029 dated Oct. 17, 2019, 27 pages.

Junghans et al. (1990) "Anti-Tac-H, a Humanized Antibody to the Interleukin 2 Receptor with New Features for Immunotherapy in Malignant and Immune Disorders", Cancer Res., 1990 50:1495-1502.

Kabat (1991) "Sequences of Proteins of Immunological Interest", National Institutes of Health, Bethesda, Md.

Kazane et al. (2012) "Synthesis of Bispecific Antibodies Using Genetically Encoded Unnatural Amin Acids", J. Am. Chem. Soc. [Epub: Dec. 4, 2012].

Klein et al. (2012) "Progress in Overcoming the Chain Association Issue in Bispecific Heterodimeric IgG Antibodies", MAbs 4(6):653-663.

Kufer et al. (2004) "A Revival of Bispecific Antibodies", Trends Biotechnol., 22:238-244.

Langer (1990) "New Methods of Drug Delivery", Science, 249:1527-1533.

Marasco et al. (2007) "The Growth and Potential of Human Antiviral Monoclonal Antibody Therapeutics", Nature Biotechnology, 25: 1421-1434.

Martin et al. (1989) "Modeling Antibody Hypervariable Loops: A Combined Algorithm", Proc. Natl. Acad. Sci. USA, 86:9268-9272.

Okuno et al. (1993) "A Common Neutralizing Epitope Conserved Between the Hemagglutinins of Influenza A Virus H1 and H2 Strains", J. Virol., 67(5):2552-2558.

Pearson (1994) "Using the FASTA Program to Search Protein and DNA Sequence Databases", Methods Mol. Biol., 24: 307-331.

Pearson (2000) "Flexible Sequence Similarity Searching with the FASTA3 Program Package", Methods in Molecular Biology, 132:185-219.

Powell et al. (1998) "Compendium of excipients for parenteral formulations", PDA J Pharm Sci Technol, 52:238-311.

Reddy et al. (2000) "Elimination of Fc Receptor-Dependent Effector Functions of a Modified IgG4 Monoclonal Antibody to Human CD4", J. Immunol., 164:1925-1933.

Reineke (2004) "Antibody Epitope Mapping Using Arrays of Synthetic Peptides" Methods Mol. Biol., 248: 443-63.

Sui et al. (2009) "Structural and Functional Bases for Broad-Spectrum Neutralization of Avian and Human Influenza A Viruses", Nature Struct. and Mol. Biol., 16(3):265-273.

Tharakaraman et al. (2015) "A Broadly Neutralizing Human Monoclonal Antibody is Effective Against H7N9", Proc Natl Acad Science, 112 (35):10890-10895.

Throsby et al. (2008) "Heterosubtypic Neutralizing Monoclonal Antibodies Cross-Protective Against H5N1 and H1N1 Recovered From Human IgM+ Memory B Cells", PLOS one, 3(2):e3942.

(56) References Cited

OTHER PUBLICATIONS

Tomer (2000) "Characterization of a Discontinuous Epitope of the Human Immunodeficiency Virus (HIV) Core Protein P24 by Epitope Excision and Differential Chemical Modification Followed by Mass Spectrometric Peptide Mapping Analysis", Prot. Sci., 9(3): 487-496.
Tutt et al. (1991) "Trispecific F(ab')3 Deivatives That Use Cooperative Signaling via the TCR/CD3 Complex and CD2 to Activate and Redirect Resting Cytotoxic T Cells", J. Immunol., 147:60-69.
Vajdos et al. (2002) "Comprehensive Functional Maps of the Antigen-Binding Site of an Anti-ErbB2 Antibody Obtained with Shotgun Scanning Mutagenesis", J Mol Biol, 320:415-428.
Wu et al. (1987) "Receptor-mediated in Vitro Gene Transformation by a Soluble DNA Carrier System", J. Biol. Chem., 262:4429-4432.
GenBank accession No. ACF41911.1 (2008).
GenBank accession No. AAR02640.1 (2016).
Antibodies, Harlow and Lane (2014) (Cold Spring Harbor Press, Cold Spring Harbor, NY).
Lloyd (1999) The Art, Science and Technology of Pharmaceutical Compounding.

\* cited by examiner

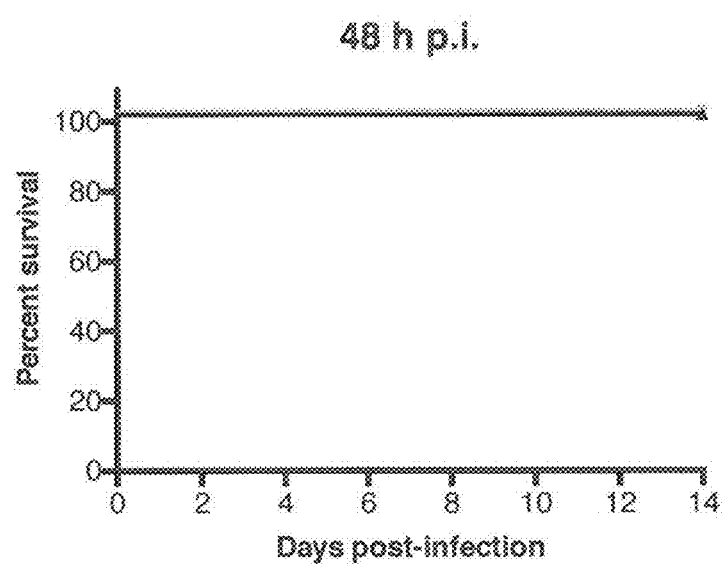

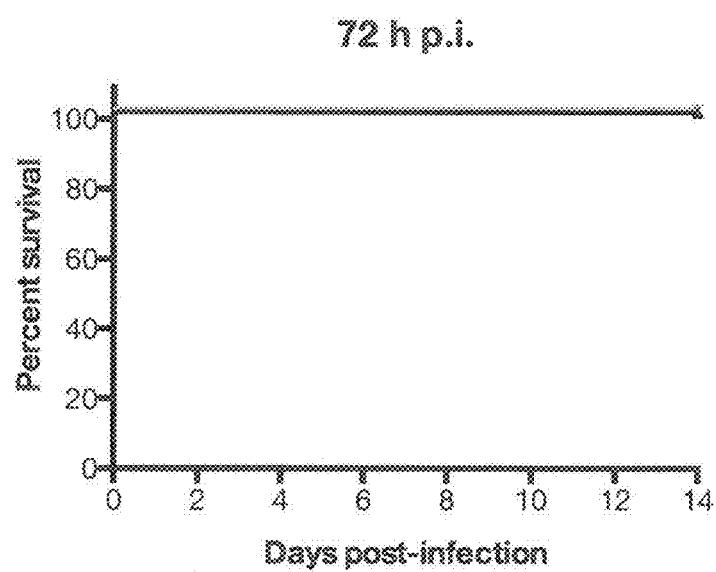

SEQUENCE LISTING

<160> NUMBER OF SEQ ID NOS: 34

<210> SEQ ID NO 1
<211> LENGTH: 360
<212> TYPE: DNA
<213> ORGANISM: Artificial Sequence
<220> FEATURE:
<223> OTHER INFORMATION: synthetic

<400> SEQUENCE: 1

```
gaggtgcagc tggtggagtc tgggggaggc ctggtcaagc cggggggtc cctgagactc      60 tcctgtgcag cctctggatt caccttcagt ggttttagca tgaactgggt ccgccaggtt     120
ccagggaagg gctggagtg gtctcatcc attagtacta gtggtaatta catgtactac      180
gcagactcag tgaagggccg attcaccatc tccagagaca cgccaagaa gtcattctct     240 ctgcaaatga acagcctgag agccgaggac tcggctatat attactgtgc gagagggggg     300
gggtataact ggaacctctt tgactactgg ggccagggtt ccctggtcac cgtctcctca     360
```

<210> SEQ ID NO 2
<211> LENGTH: 120
<212> TYPE: PRT
<213> ORGANISM: Artificial Sequence
<220> FEATURE:
<223> OTHER INFORMATION: synthetic

<400> SEQUENCE: 2

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Gly Phe
            20                  25                  30

Ser Met Asn Trp Val Arg Gln Val Pro Gly Lys Gly Leu Glu Trp Val
        35                  40                  45

Ser Ser Ile Ser Thr Ser Gly Asn Tyr Met Tyr Tyr Ala Asp Ser Val
    50                  55                  60

Lys Gly Arg Phe Thr Ile Ser Arg Asp Asn Ala Lys Lys Ser Phe Ser
65                  70                  75                  80

Leu Gln Met Asn Ser Leu Arg Ala Glu Asp Ser Ala Ile Tyr Tyr Cys
                85                  90                  95

Ala Arg Gly Gly Gly Tyr Asn Trp Asn Leu Phe Asp Tyr Trp Gly Gln
            100                 105                 110

Gly Ser Leu Val Thr Val Ser Ser
        115                 120
```

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3

```
ggattcacct tcagtggttt tagc                                             24
```

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

```
Gly Phe Thr Phe Ser Gly Phe Ser
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
attagtacta gtggtaatta catg                                              24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Ser Thr Ser Gly Asn Tyr Met
1               5

<210> SEQ ID NO 7
<211> LENGTH: 39
<212> TYPE: DNA
<213> ORGANISM: Artificial Sequence
<220> FEATURE:
<223> OTHER INFORMATION: synthetic

<400> SEQUENCE: 7
gcgagagggg gggggtataa ctggaacctc tttgactac                              39

<210> SEQ ID NO 8
<211> LENGTH: 13
<212> TYPE: PRT
<213> ORGANISM: Artificial Sequence
<220> FEATURE:
<223> OTHER INFORMATION: synthetic

<400> SEQUENCE: 8

Ala Arg Gly Gly Gly Tyr Asn Trp Asn Leu Phe Asp Tyr
1               5                   10

<210> SEQ ID NO 9
<211> LENGTH: 324
<212> TYPE: DNA
<213> ORGANISM: Artificial Sequence
<220> FEATURE:
<223> OTHER INFORMATION: synthetic

<400> SEQUENCE: 9
gaaattgtgt tgacgcagtc tccaggcacc ctgtctttgt ctccagggga aagagccacc       60
ctctcctgca gggccagtca gagtcttaac agcaactact tagcctggta ccagcagaaa      120
cctggccagg ctcccagact cctcatctat ggtgcatcca gcagggccac tggcatccca      180
gacaggttca gtggcagtgg gtctgggaca gacttcactc tcaccatcac cagactggag      240
tctgaagatt ttgcagtata ttactgtcag caatatggta actccccgct cactttcggc      300
ggagggacca aggtggagat caaa                                             324

<210> SEQ ID NO 10
<211> LENGTH: 108
```

```
<212> TYPE: PRT
<213> ORGANISM: Artificial Sequence
<220> FEATURE:
<223> OTHER INFORMATION: synthetic

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Asn Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Thr Arg Leu Glu
65                  70                  75                  80

Ser Glu Asp Phe Ala Val Tyr Tyr Cys Gln Gln Tyr Gly Asn Ser Pro
                85                  90                  95

Leu Thr Phe Gly Gly Gly Thr Lys Val Glu Ile Lys
            100                 105

<210> SEQ ID NO 11
<211> LENGTH: 21
<212> TYPE: DNA
<213> ORGANISM: Artificial Sequence
<220> FEATURE:
<223> OTHER INFORMATION: synthetic

<400> SEQUENCE: 11
cagagtctta acagcaacta c                                        21

<210> SEQ ID NO 12
<211> LENGTH: 7
<212> TYPE: PRT
<213> ORGANISM: Artificial Sequence
<220> FEATURE:
<223> OTHER INFORMATION: synthetic

<400> SEQUENCE: 12

Gln Ser Leu Asn Ser Asn Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 ggtgcatcc                                                       9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Gly Ala Ser
1
```

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
cagcaatatg gtaactcccc gctcact                                     27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Gln Tyr Gly Asn Ser Pro Leu Thr
1               5

<210> SEQ ID NO 17
<211> LENGTH: 360
<212> TYPE: DNA
<213> ORGANISM: Artificial Sequence
<220> FEATURE:
<223> OTHER INFORMATION: synthetic

<400> SEQUENCE: 17
gaggtgcagc tggtggagtc tgggggaggc ctggtcaagc cgggggggtc cctgagactc    60
tcctgtgcag cctctggatt cagtttcagt ggttttagca tgaactgggt ccgccaggct   120
ccagggaagg ggctggagtg ggtctcatcc attagtacta gtggtaatta catgtactac   180
gcagactcag tgaagggccg attcaccatc tccagagaca cgccaagaa gtcattctct   240 ctgcaaatga acagcctgag agccgaggac tcggctatat attactgtgc gagaggggggg   300 gggtataact ggaacctctt tgactactgg ggccagggtt ccctggtcac cgtctcctca   360

<210> SEQ ID NO 18
<211> LENGTH: 120
<212> TYPE: PRT
<213> ORGANISM: Artificial Sequence
<220> FEATURE:
<223> OTHER INFORMATION: synthetic

<400> SEQUENCE: 18

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Gly Phe
            20                  25                  30

Ser Met Asn Trp Val Arg Gln Ala Pro Gly Lys Gly Leu Glu Trp Val
        35                  40                  45

Ser Ser Ile Ser Thr Ser Gly Asn Tyr Met Tyr Tyr Ala Asp Ser Val
    50                  55                  60

Lys Gly Arg Phe Thr Ile Ser Arg Asp Asn Ala Lys Lys Ser Phe Ser
65                  70                  75                  80

Leu Gln Met Asn Ser Leu Arg Ala Glu Asp Ser Ala Ile Tyr Tyr Cys
                85                  90                  95

Ala Arg Gly Gly Gly Tyr Asn Trp Asn Leu Phe Asp Tyr Trp Gly Gln
            100                 105                 110

Gly Ser Leu Val Thr Val Ser Ser
        115                 120

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcagtt tcagtggttt tagc                                          24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Phe Ser Phe Ser Gly Phe Ser
1               5

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
attagtacta gtggtaatta catg                                          24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Ser Thr Ser Gly Asn Tyr Met
1               5

<210> SEQ ID NO 23
<211> LENGTH: 39
<212> TYPE: DNA
<213> ORGANISM: Artificial Sequence
<220> FEATURE:
<223> OTHER INFORMATION: synthetic

<400> SEQUENCE: 23
gcgagagggg gggggtataa ctggaacctc tttgactac                          39

<210> SEQ ID NO 24
<211> LENGTH: 13
<212> TYPE: PRT
<213> ORGANISM: Artificial Sequence
<220> FEATURE:
<223> OTHER INFORMATION: synthetic

<400> SEQUENCE: 24

Ala Arg Gly Gly Gly Tyr Asn Trp Asn Leu Phe Asp Tyr
1               5                   10

<210> SEQ ID NO 25
<211> LENGTH: 324

```
<212> TYPE: DNA
<213> ORGANISM: Artificial Sequence
<220> FEATURE:
<223> OTHER INFORMATION: synthetic

<400> SEQUENCE: 25
gaaattgtgt tgacgcagtc tccaggcacc ctgtctttgt ctccagggga aagagccacc    60
ctctcctgca gggccagtca gagtcttaac agcaactact tagcctggta ccagcagaaa   120
cctggccagg ctcccagact cctcatctat ggtgcatcca gcagggccac tggcatccca   180
gacaggttca gtggcagtgg gtctgggca gacttcactc tcaccatcag cagactggag    240
tctgaagatt ttgcagtgta ttactgtcag caatatggta actccccgct cactttcggc   300
ggagggacca aggtggagat caaa                                          324

<210> SEQ ID NO 26
<211> LENGTH: 108
<212> TYPE: PRT
<213> ORGANISM: Artificial Sequence
<220> FEATURE:
<223> OTHER INFORMATION: synthetic

<400> SEQUENCE: 26

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Leu Asn Ser Asn
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Ala Asp Phe Thr Leu Thr Ile Ser Arg Leu Glu
 65                  70                  75                  80

Ser Glu Asp Phe Ala Val Tyr Tyr Cys Gln Gln Tyr Gly Asn Ser Pro
                 85                  90                  95

Leu Thr Phe Gly Gly Gly Thr Lys Val Glu Ile Lys
            100                 105

<210> SEQ ID NO 27
<211> LENGTH: 21
<212> TYPE: DNA
<213> ORGANISM: Artificial Sequence
<220> FEATURE:
<223> OTHER INFORMATION: synthetic

<400> SEQUENCE: 27
cagagtctta acagcaacta c                                              21

<210> SEQ ID NO 28
<211> LENGTH: 7
<212> TYPE: PRT
<213> ORGANISM: Artificial Sequence
<220> FEATURE:
<223> OTHER INFORMATION: synthetic

<400> SEQUENCE: 28

Gln Ser Leu Asn Ser Asn Tyr
 1               5

<210> SEQ ID NO 29
<211> LENGTH: 9
<212> TYPE: DNA
```

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 ggtgcatcc                                                                 9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Gly Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
cagcaatatg gtaactcccc gctcact                                            27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Gln Gln Tyr Gly Asn Ser Pro Leu Thr
1               5

<210> SEQ ID NO 33
<211> LENGTH: 566
<212> TYPE: PRT
<213> ORGANISM: Artificial Sequence
<220> FEATURE:
<223> OTHER INFORMATION: A/Wisconsin/67/X-161/2005 (H3N2) Accession No:
      ACF41911.1 aa1-16: signal peptide aa17-566: Mature protein

<400> SEQUENCE: 33

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val

```
            115                 120                 125
Ala Ser Ser Gly Thr Leu Glu Phe Asn Asp Glu Ser Phe Asn Trp Thr
130                 135                 140
Gly Val Thr Gln Asn Gly Thr Ser Ser Cys Lys Arg Arg Ser Asn
145                 150                 155                 160
Asn Ser Phe Phe Ser Arg Leu Asn Trp Leu Thr Gln Leu Lys Phe Lys
                165                 170                 175
Tyr Pro Ala Leu Asn Val Thr Met Pro Asn Asn Glu Lys Phe Asp Lys
                180                 185                 190
Leu Tyr Ile Trp Gly Val His His Pro Val Thr Asp Asn Asp Gln Ile
                195                 200                 205
Phe Leu Tyr Ala Gln Ala Ser Gly Arg Ile Thr Val Ser Thr Lys Arg
210                 215                 220
Ser Gln Gln Thr Val Ile Pro Asn Ile Gly Ser Arg Pro Arg Ile Arg
225                 230                 235                 240
Asn Ile Pro Ser Arg Ile Ser Ile Tyr Trp Thr Ile Val Lys Pro Gly
                245                 250                 255
Asp Ile Leu Leu Ile Asn Ser Thr Gly Asn Leu Ile Ala Pro Arg Gly
                260                 265                 270
Tyr Phe Lys Ile Arg Ser Gly Lys Ser Ser Ile Met Arg Ser Asp Ala
                275                 280                 285
Pro Ile Gly Lys Cys Asn Ser Glu Cys Ile Thr Pro Asn Gly Ser Ile
290                 295                 300
Pro Asn Asp Lys Pro Phe Gln Asn Val Asn Arg Ile Thr Tyr Gly Ala
305                 310                 315                 320
Cys Pro Arg Tyr Val Lys Gln Asn Thr Leu Lys Leu Ala Thr Gly Met
                325                 330                 335
Arg Asn Val Pro Glu Lys Gln Thr Arg Gly Ile Phe Gly Ala Ile Ala
                340                 345                 350
Gly Phe Ile Glu Asn Gly Trp Glu Gly Met Val Asp Gly Trp Tyr Gly
                355                 360                 365
Phe Arg His Gln Asn Ser Glu Gly Ile Gly Gln Ala Ala Asp Leu Lys
                370                 375                 380
Ser Thr Gln Ala Ala Ile Asn Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
                420                 425                 430
Lys Ile Asp Leu Trp Ser Tyr Asn Ala Glu Leu Leu Val Ala Leu Glu
                435                 440                 445
Asn Gln His Thr Ile Asp Leu Thr Asp Ser Glu Met Asn Lys Leu Phe
                450                 455                 460
Glu Arg Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
                500                 505                 510
Asn Asn Arg Phe Gln Ile Lys Gly Val Glu Leu Lys Ser Gly Tyr Lys
                515                 520                 525
Asp Trp Ile Leu Trp Ile Ser Phe Ala Ile Ser Cys Phe Leu Leu Cys
                530                 535                 540
```

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 34
<211> LENGTH: 549
<212> TYPE: PRT
<213> ORGANISM: Artificial Sequence
<220> FEATURE:
<223> OTHER INFORMATION: A/chicken/Netherlands/01/2003 (H7N7) Accession
      No. AAR02640.1 aa1-18: signal peptide aa19-538: Mature protein

<400> SEQUENCE: 34

Met Asn Thr Gln Ile Leu Val Phe Ala Leu Val Ala Ser Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
            35                  40                  45

Glu Thr Val Glu Arg Thr Asn Val Pro Arg Ile Cys Ser Lys Gly Lys
        50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Thr Met Gly Phe Thr Tyr Ser Gly Ile Arg Thr Asn Gly Thr Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Asp Pro Ala Leu Ile Ile Trp Gly Ile His
            180                 185                 190

His Ser Gly Ser Thr Thr Glu Gln Thr Lys Leu Tyr Gly Ser Gly Asn
        195                 200                 205

Lys Leu Ile Thr Val Gly Ser Ser Asn Tyr Gln Gln Ser Phe Val Pro
210                 215                 220

Ser Pro Gly Ala Arg Pro Gln Val Asn Gly Gln Ser Gly Arg Ile Asp
225                 230                 235                 240

Phe His Trp Leu Ile Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Glu Val Gln Val Asp Ala Asn Cys Glu Gly
        275                 280                 285

Asp Cys Tyr His Ser Gly Gly Thr Ile Ile Ser Asn Leu Pro Phe Gln
290                 295                 300

Asn Ile Asn Ser Arg Ala Val Gly Lys Cys Pro Arg Tyr Val Lys Gln
305                 310                 315                 320

Glu Ser Leu Leu Leu Ala Thr Gly Met Lys Asn Val Pro Glu Ile Pro

-continued

```
                325                 330                 335
Lys Arg Arg Arg Arg Gly Leu Phe Gly Ala Ile Ala Gly Phe Ile Glu
            340                 345                 350

Asn Gly Trp Glu Gly Leu Ile Asp Gly Trp Tyr Gly Phe Arg His Gln
            355                 360                 365

Asn Ala Gln Gly Glu Gly Thr Ala Ala Asp Tyr Lys Ser Thr Gln Ser
            370                 375                 380

Ala Ile Asp Gln Ile Thr Gly Lys Leu Asn Arg Leu Ile Glu Lys Thr
385                 390                 395                 400

Asn Gln Gln Phe Glu Leu Ile Asp Asn Glu Phe Thr Glu Val Glu Arg
                405                 410                 415

Gln Ile Gly Asn Val Ile Asn Trp Thr Arg Asp Ser Met Thr Glu Val
            420                 425                 430

Trp Ser Tyr Asn Ala Glu Leu Leu Val Ala Met Glu Asn Gln His Thr
            435                 440                 445

Ile Asp Leu Ala Asp Ser Glu Met Asn Lys Leu Tyr Glu Arg Val Lys
            450                 455                 460

Arg Gln Leu Arg Glu Asn Ala Glu Glu Asp Gly Thr Gly Cys Phe Glu
465                 470                 475                 480

Ile Phe His Lys Cys Asp Asp Cys Met Ala Ser Ile Arg Asn Asn
                485                 490                 495

Thr Tyr Asp His Ser Lys Tyr Arg Glu Glu Ala Ile Gln Asn Arg Ile
            500                 505                 510

Gln Ile Asp Pro Val Lys Leu Ser Ser Gly Tyr Lys Asp Val Ile Leu
            515                 520                 525

Trp Phe Ser Phe Gly Ala Ser Cys Phe Ala His His His His His His
            530                 535                 540

His His His His Tyr
545
```

HUMAN ANTIBODIES TO INFLUENZA HEMAGGLUTININ

CROSS-REFERENCE TO RELATED APPLICATIONS

This Application is a National Stage Application of PCT/US2019/015029, filed Jan. 24, 2019, which claims the benefit under 35 USC § 119(e) of U.S. provisional patent application no. 62/622,480, filed Jan. 26, 2018; each of which is herein incorporated by reference in its entirety for all purposes. To the extent appropriate, a claim of priority is made of each of the above-disclosed applications.

FIELD OF THE INVENTION

The present invention is related to human antibodies and antigen-binding fragments thereof that specifically bind to influenza A group 2 hemagglutinin (HA), compositions comprising these antibodies and therapeutic and diagnostic methods of using these antibodies.

SEQUENCE LISTING

An official copy of the sequence listing is submitted concurrently with the specification electronically via EFS-Web as an ASCII formatted sequence listing with a file name of "10201WO01_SEQ_LIST.txt", a creation date of Jan. 24, 2019, and a size of about 21 KB. The sequence listing contained in this ASCII formatted document is part of the specification and is herein incorporated by reference in its entirety.

BACKGROUND OF THE INVENTION

Influenza is a highly contagious disease, which has a long history characterized by waves of pandemics, epidemics, resurgences and outbreaks. In spite of annual vaccination efforts, influenza infections result in substantial morbidity and mortality.

Influenza viruses consist of three types, A, B and C. Furthermore, influenza A viruses can be classified into subtypes based on allelic variations in antigenic regions of two genes that encode the surface glycoproteins, hemagglutinin (HA) and neuraminidase (NA), which are required for viral attachment and entry into the host cell.

Hemagglutinin is a trimeric glycoprotein that contains two structural domains, a globular head domain that consists of the receptor-binding site (that is subject to frequent antigenic drift) and the stem region (more conserved among various strains of influenza virus). The HA protein is synthesized as a precursor (HA0), which undergoes proteolytic processing to produce two subunits (HA1 and HA2), which associate with one another to form the stem/globular head structure. The HA1 peptide is responsible for the attachment of virus to the cell surface. The HA2 peptide forms a stem-like structure that mediates the fusion of viral and cell membranes in endosomes, allowing the release of the ribonucleoprotein complex into the cytoplasm.

Currently, there are eighteen subtypes defined by their hemagglutinin proteins (H1-H18). The 18 HAs can be classified into two groups. Group 1 consists of H1, H2, H5, H6, H8, H9, H11, H12, H13, H16, H17 and H18 subtypes, and group 2 includes H3, H4, H7, H10, H14 and H15 subtypes.

New strains of the same subtype may arise as a result of a phenomenon called antigenic drift, or mutations in the HA or NA molecules which generate new and different epitopes. A consequence of this is that a new vaccine must be produced every year against viruses that are predicted to emerge, a process that is not only costly, but highly inefficient. While technological advances have improved the ability to produce improved influenza antigen(s) for vaccine compositions, there remains a need to provide additional sources of protection to address emerging subtypes and strains of influenza.

While the idea of a vaccine composition comprising the antigen of interest (e.g. the HA and/or NA) to generate broadly neutralizing antibodies in a patient is generally thought to be a good approach, it is not always desirable to use this approach in certain patient populations. For example, in certain patients, a vaccine composition comprising the antigen of interest may not always be effective, such as in the elderly, in the very young, in immunocompromised patients, etc. In these patient populations, or in any patient who is not able to mount an effective immune response, it may be more beneficial to provide a composition already containing broadly neutralizing antibodies that may target epitopes common to a variety of strains within Group 1 and/or Group 2 subtypes.

To date there has been limited success in identifying such antibodies that broadly neutralize or inhibit influenza viruses. Okuno et al. immunized mice with influenza A/Okuda/57 (H2N2) and isolated an antibody designated C179, which bound to a conserved conformational epitope in HA2 and neutralized the Group 1 H2, H1 and H5 subtype influenza A viruses in vitro and in vivo (Okuno et al. (1993) J. Virol. 67(5):2552-2558). Throsby et al. identified 13 monoclonal antibodies from human B cells that had broad activity against Group 1 subtypes (Throsby et al. (2008), PLOS one 3(2):e3942). Sui et al. identified a human monoclonal antibody (F10), which bound H5 and other Group 1 viruses (Sui, et al. (2009), Nat. Struct. Mol. Biol. 16(3):265-273). Tharakaraman et al. identified a broadly neutralizing antibody designated VIS410, which was effective in neutralizing group 2 strains of influenza virus, including H3N2 and H7N9 strains, in vitro and in vivo (Tharakaraman, K, et al., (2015), Proc Natl Acad Science 112 (35):10890-10895).

However, after decades of research in this area, only a few antibodies are currently in clinical trials to assess their ability to neutralize influenza viruses of different subtypes (See, for example, antibodies under development by Crucell Holland ((US2012/0276115, US2014/0065156, U.S. Pat. No. 8,470,327, US2014/0120113, EP2731967, U.S. Pat. No. 8,691,223, US2013/0243792, US2014/0065165, WO2008/028946 and WO2010/130636); Osaka University (US2011/0319600, EP2380976, US2012/0058124, US2012/0058124), Celltrion (US2013/0004505, EP2545074; WO2014/158001); Vanderbilt University (US2013/0289246), SeaLane Biotechnologies (US2012/0128671), Trellis Bioscience, Inc. (US2012/0020971 EP2582721); Visterra, Inc. (US2013/0302349); Burnham Institute/Dana Farber (US2014/011982, EP2222701, WO2010/027818); Temasek (U.S. Pat. Nos. 8,444,986, 8,574,581, 8,637,644, 8,637,645, 8,383,121, 8,540,996, 8,574,830, 8,540,995); HUMABS Biosciences/Institute for Research in Biomedicine (U.S. Pat. Nos. 8,871,207, 8,685,402, EP2313433); MedImmune (WO2015/051010); AIMM Therapeutics (WO2013/081463, EP12798020) and Genentech (US2014/0161822), but there are still no marketed antibodies that broadly neutralize or inhibit influenza A virus infection or attenuate the disease caused by various subtypes of this virus. Accordingly, there is still a need in the art to identify new antibodies that neutralize multiple subtypes of influenza A virus, which can be used to prevent or treat an influenza virus infection.

BRIEF SUMMARY OF THE INVENTION

The present invention provides antibodies and antigen-binding fragments thereof that bind influenza A group 2 hemagglutinin (HA). The antibodies of the present invention are useful, inter alia, for inhibiting or neutralizing the activity of influenza A group 2 HA. In some embodiments, the antibodies are useful for blocking attachment of the influenza virus to the host cell and/or for preventing the entry of the influenza virus into host cells. In some embodiments, the antibodies function by inhibiting the cell-to-cell transmission of the virus. In certain embodiments, the antibodies are useful in preventing, treating or ameliorating at least one symptom of influenza virus infection in a subject. In certain embodiments, the antibodies may be administered prophylactically or therapeutically to a subject having, or at risk of acquiring, an influenza virus infection. In certain embodiments, compositions containing at least one antibody of the invention may be administered to a subject for whom a vaccine is contra-indicated, or for whom a vaccine is less efficacious, for example, an elderly patient, a very young patient, a patient who may be allergic to any one or more components of a vaccine, or an immunocompromised patient who may be non-responsive to the immunogens in a vaccine. In certain embodiments, compositions containing at least one antibody of the invention may be administered to medical staff, hospitalized patients or nursing home residents or other high-risk patients during an influenza outbreak. In certain embodiments, compositions containing at least one antibody of the invention may be administered as a first line treatment to patients in the event that a predicted yearly vaccine is ineffective, or in the event of a pandemic with a strain that has undergone a major antigenic shift.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to increase persistence in the host or to increase effector function or eliminate residual effector functions (Reddy et al., 2000, J. Immunol. 164:1925-1933). In certain embodiments, the antibodies may be bispecific.

In a first aspect, the present invention provides isolated recombinant monoclonal antibodies or antigen-binding fragments thereof that bind specifically to influenza A group 2 hemagglutinin (HA).

In one embodiment, the present invention provides an isolated recombinant antibody or antigen-binding fragment thereof that specifically binds to influenza A group 2 HA, wherein the antibody has two or more of the following characteristics:

(a) is a fully human monoclonal antibody;

(b) binds to influenza A group 2 HA with a dissociation constant (K$_D$) of less than $10^{-8}$M, as measured by surface plasmon resonance;

(c) demonstrates a dissociative half-life (t½) greater than 75 minutes;

(d) demonstrates neutralization of influenza A group 2 viruses selected from H3N2 and H7N9 strains with an IC$_{50}$ of less than 200 nM and 500 nM, respectively;

(e) demonstrates complement mediated lysis of influenza virus infected cells with an EC$_{50}$ of less than about 150 nM;

(f) demonstrates antibody-dependent cell-mediated cytotoxicity of virus infected target cells using a reporter bioassay with an EC$_{50}$ of less than about 0.9 nM;

(g) demonstrates antibody-dependent cell-mediated cytotoxicity of virus infected target cells in the presence of human peripheral blood mononuclear cells (PBMC) with an EC$_{50}$ of less than about 0.180 nM;

(h) demonstrates an increase in survival in an influenza-infected animal when administered at 24, 48, 72, or 96 hours after virus challenge;

(i) demonstrates an increase in survival in an influenza-infected animal when administered in combination with oseltamivir at 96 hours after infection; or (j) wherein the antibody or antigen-binding fragment thereof comprises three heavy chain complementarity determining regions (CDRs) (HCDR1, HCDR2 and HCDR3) contained within any one of the heavy chain variable region (HCVR) sequences listed in Table 1; and three light chain CDRs (LCDR1, LCDR2 and LCDR3) contained within any one of the light chain variable region (LCVR) sequences listed in Table 1.

In certain embodiments, an antibody of the invention demonstrates an increase in protection when administered to an influenza virus infected mammal as a single intravenous dose of about 7 to 15 mg/kg starting at day 3 post-infection compared to oral administration of oseltamivir administered twice daily for 5 days at a dose of about 2 mg/kg starting at day 3 post-infection (and continuing until day 7 post-infection).

In a related embodiment, an antibody of the invention confers an increase in protection in a mammal infected with influenza virus when administered either subcutaneously or intravenously and/or when administered prior to infection, or after infection with influenza virus.

In one embodiment, an antibody of the invention demonstrates an increase in protection, as compared to an animal administered an isotype (negative) control antibody, when administered to an infected mammal as a single subcutaneous or intravenous dose ranging from about 5 mg/kg to about 15 mg/kg.

In one embodiment, an antibody of the invention demonstrates an increase in protection when administered to an influenza virus infected mammal as a single intravenous dose of about 7 mg/kg to about 15 mg/kg compared to oral administration of oseltamivir administered twice daily for 5 days at a dose of about 2 mg/kg.

In one embodiment, an antibody of the invention demonstrates a survival rate of about 100% in a mammal infected with influenza virus, when administered as a single dose of about 15 mg/kg at 24 hours or longer post infection.

In one embodiment, an antibody of the invention demonstrates a survival rate of 100% in a mammal infected with influenza virus, when administered as a single intravenous dose of about 15 mg/kg at 24, 48, 72, or 96 hours post infection.

In one embodiment, an antibody of the invention demonstrates a survival rate of about 100% in a mammal infected with influenza virus, when administered as a single intravenous dose of about 15 mg/kg compared to an 80% survival rate observed with oseltamivir when administered orally twice a day for 5 days at a dose of about 2 mg/kg.

In one embodiment, an antibody of the invention provides an additive protective effect in a mammal infected with influenza virus when administered with oseltamivir at greater than 48 hours post infection.

In one embodiment, an antibody of the invention provides an additive protective effect in a mammal infected with influenza virus when administered with oseltamivir at 72 hours post infection.

In one embodiment, an antibody of the invention provides an additive protective effect when used in combination with oseltamivir when the antibody is administered to an influenza virus infected mammal as a single intravenous dose ranging from about 7 mg/kg to about 15 mg/kg and the oseltamivir is administered orally twice daily for 5 days at a dose of about 2 mg/kg.

In a related embodiment, an antibody of the invention provides an additive protective effect when used in combination with oseltamivir at 96 hours after influenza virus infection, wherein the antibody is administered as a single intravenous dose ranging from about 7 mg/kg to about 15 mg/kg and the oseltamivir is administered orally twice daily for 5 days at a dose of about 2 mg/kg.

In one embodiment, an antibody of the invention may be administered intravenously, intranasally, subcutaneously, intradermally, or intramuscularly and the oseltamivir may be administered orally.

In one embodiment, the oseltamivir is administered prior to, concurrently with, or after administration of an antibody of the invention.

In one embodiment, the antibody and/or the oseltamivir may be administered as a single dose, or as multiple doses.

Exemplary anti-influenza A group 2 HA antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of exemplary anti-influenza HA antibodies. Table 2 sets forth the nucleic acid sequence identifiers of the HCVRs, LCVRs, HCDR1, HCDR2 HCDR3, LCDR1, LCDR2 and LCDR3 of the exemplary anti-influenza HA antibodies.

The present invention provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

In one embodiment the invention provides antibodies, or antigen-binding fragments thereof, which specifically bind influenza A group 2 HA, comprising a HCVR having an amino acid sequence of SEQ ID NOs: 2 or 18.

The present invention also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

In one embodiment the invention provides antibodies, or antigen-binding fragments thereof, which specifically bind influenza A group 2 HA, comprising a LCVR having an amino acid sequence of SEQ ID NOs: 10, or 26.

In one embodiment, the isolated antibody or antigen-binding fragment that specifically binds influenza A group 2 HA comprises a HCVR/LCVR amino acid sequence pair selected from the group consisting of SEQ ID NOs: 2/10, or 18/26.

In certain embodiments, the HCVR/LCVR amino acid sequence pair is selected from the group consisting of SEQ ID NOs: 2/10 (e.g., H1H14611N2) or 18/26 (e.g., H1H14612N2).

In one embodiment, the isolated antibody or antigen-binding fragment comprises: (a) a HCDR1 domain having an amino acid sequence selected from the group consisting of SEQ ID NOs: 4, or 20;

(b) a HCDR2 domain having an amino acid sequence selected from the group consisting of SEQ ID NOs: 6, or 22;

(c) a HCDR3 domain having an amino acid sequence selected from the group consisting of SEQ ID NOs: 8, or 24;

(d) a LCDR1 domain having an amino acid sequence selected from the group consisting of SEQ ID NOs: 12, or 28;

(e) a LCDR2 domain having an amino acid sequence selected from the group consisting of SEQ ID NOs: 14, or 30; and (f) a LCDR3 domain having an amino acid sequence selected from the group consisting of SEQ ID NOs: 16, or 32.

In one embodiment, the isolated antibody or antigen-binding fragment, which specifically binds influenza A group 2 HA, comprises (a) a HCDR1 of SEQ ID NO: 4, (b) a HCDR2 of SEQ ID NO: 6; (c) a HCDR3 of SEQ ID NO: 8; (d) a LCDR1 of SEQ ID NO: 12; (e) a LCDR2 of SEQ ID NO: 14 and (f) a LCDR3 of SEQ ID NO: 16.

In one embodiment, the isolated antibody or antigen-binding fragment, which specifically binds influenza A group 2 HA, comprises (a) a HCDR1 of SEQ ID NO: 20, (b) a HCDR2 of SEQ ID NO: 22; (c) a HCDR3 of SEQ ID NO: 24; (d) a LCDR1 of SEQ ID NO: 28; (e) a LCDR2 of SEQ ID NO: 30 and (f) a LCDR3 of SEQ ID NO: 32.

The present invention also provides antibodies, or antigen-binding fragments thereof, comprising a heavy chain CDR1 (HCDR1) comprising an amino acid sequence selected from any of the HCDR1 amino acid sequences listed in Table 1, or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 1, or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 1, or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 1, or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 1, or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 1, or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 1, paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-influenza A group 2 HA antibodies listed in Table 1. In certain embodiments, the HCDR3/LCDR3 amino acid sequence pair is selected from the group consisting of SEQ ID NOs: 8/16 (e.g., H1H14611N2), or 24/32 (e.g., H1H14612N2).

The present invention also provides antibodies, or antigen-binding fragments thereof, comprising a set of six CDRs (i.e., HCDR1-HCDR2-HCDR3-LCDR1-LCDR2-LCDR3) contained within any of the exemplary anti-influenza A group 2 HA antibodies listed in Table 1. In certain embodiments, the HCDR1-HCDR2-HCDR3-LCDR1-LCDR2-LCDR3 amino acid sequence set is selected from the group consisting of SEQ ID NOs: 4-6-8-12-14-16 (e.g., H1H14611N2); or SEQ ID NOs: 20-22-24-28-30-32 (e.g., H1H14612N2).

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-influenza A group 2 HA antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 2/10 (e.g., H1H14611N2), or SEQ ID NOs: 18/26 (e.g., H1H14612N2). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides for antibodies and antigen-binding fragments thereof that compete for specific binding to influenza A group 2 HA with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides antibodies and antigen-binding fragments thereof that cross-compete for binding to influenza A group 2 HA, or that bind the same epitope on influenza A group 2 HA, as a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides isolated antibodies and antigen-binding fragments thereof that block influenza A group 2 HA attachment to, and/or entry into a host cell.

In certain embodiments, the antibodies or antigen-binding fragments of the present invention are bispecific comprising a first binding specificity to a first epitope in the influenza A group 2 HA and a second binding specificity to another antigen.

In a second aspect, the present invention provides nucleic acid molecules encoding anti-influenza A group 2 HA antibodies or portions thereof. For example, the present invention provides nucleic acid molecules encoding any of the HCVR amino acid sequences listed in Table 2; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-influenza HA antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-influenza HA antibodies listed in Table 1.

The present invention also provides nucleic acid molecules encoding both an HCVR and an LCVR, wherein the HCVR comprises an amino acid sequence of any of the HCVR amino acid sequences listed in Table 1 and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-influenza A group 2 HA antibody listed in Table 1.

The present invention provides nucleic acid molecules encoding any of the heavy chain amino acid sequences listed in Table 1. The present invention also provides nucleic acid molecules encoding any of the light chain amino acid sequences listed in Table 1.

In a related aspect, the present invention provides recombinant expression vectors capable of expressing a polypeptide comprising a heavy or light chain variable region of an anti-influenza A group 2 HA antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In a third aspect, the invention provides a pharmaceutical composition comprising a therapeutically effective amount of at least one recombinant monoclonal antibody or antigen-binding fragment thereof which specifically binds influenza A group 2 HA and a pharmaceutically acceptable carrier. In a related aspect, the invention features a composition, which is a combination of an anti-influenza A group 2 HA antibody and a second therapeutic agent. In one embodiment, the second therapeutic agent is any agent that is advantageously combined with an anti-influenza A group 2 HA antibody. Exemplary agents that may be advantageously combined with an anti-influenza A group 2 HA antibody include, without limitation, other agents that bind and/or inhibit influenza HA activity (including other antibodies or antigen-binding fragments thereof, etc.) and/or agents, which do not directly bind influenza HA but nonetheless inhibit viral activity including infectivity of host cells. In certain embodiments, the invention provides for a pharmaceutical composition comprising: (a) a first anti-influenza A group 2 HA antibody or antigen-binding fragment thereof; (b) a second anti-influenza A group 2 HA antibody or antigen-binding fragment thereof, wherein the first antibody binds to a first epitope on influenza A group 2 HA and the second antibody binds to a second epitope on influenza A group 2 HA wherein the first and second epitopes are distinct and non-overlapping; and (c) a pharmaceutically acceptable carrier or diluent. In certain embodiments, the invention provides for a pharmaceutical composition comprising: (a) a first anti-influenza A group 2 HA antibody or antigen-binding fragment thereof; (b) a second anti-influenza A group 2 HA antibody or antigen-binding fragment thereof, wherein the first antibody does not cross-compete with the second antibody for binding to influenza A group 2 HA; and (c) a pharmaceutically acceptable carrier or diluent. In certain embodiments, the invention provides for a pharmaceutical composition comprising: (a) a first anti-influenza A group 2 HA antibody or antigen-binding fragment thereof; (b) a second anti-influenza antibody or antigen-binding fragment thereof, which interacts with a different influenza antigen, wherein the first antibody binds to an epitope on influenza A group 2 HA and the second antibody binds to an epitope on a different influenza antigen; and (c) a pharmaceutically acceptable carrier or diluent. In certain embodiments, the invention provides for a pharmaceutical composition comprising: (a) a first anti-influenza A group 2 HA antibody or antigen-binding fragment thereof; (b) a second antibody or antigen-binding fragment thereof, which interacts with a different viral (non-influenza) antigen, wherein the first antibody binds to an epitope on influenza A group 2 HA and the second antibody binds to an epitope on a different viral (non-influenza) antigen; and (c) a pharmaceutically acceptable carrier or diluent. Additional combination therapies and co-formulations involving the anti-influenza A group 2 HA antibodies of the present invention are disclosed elsewhere herein.

In a fourth aspect, the invention provides therapeutic methods for treating a disease or disorder associated with influenza A group 2 HA (such as viral infection in a subject), or at least one symptom associated with the viral infection, using an anti-influenza A group 2 HA antibody or antigen-binding portion of an antibody of the invention, wherein the therapeutic methods comprise administering a therapeutically effective amount of a pharmaceutical composition comprising an antibody or antigen-binding fragment of an antibody of the invention to the subject in need thereof. The disorder treated is any disease or condition, which is improved, ameliorated, inhibited or prevented by inhibition of influenza HA activity. In certain embodiments, the invention provides methods to prevent, treat or ameliorate at least one symptom of influenza A infection, the method comprising administering a therapeutically effective amount of an anti-influenza HA antibody or antigen-binding fragment thereof of the invention to a subject in need thereof.

In some embodiments, the present invention provides methods to ameliorate or reduce the severity, duration, or frequency of occurrence, of at least one symptom of influenza infection in a subject by administering an anti-influenza A group 2 HA antibody of the invention, wherein the at least one symptom is selected from the group consisting of headache, fever, aches, rhinorrhea (nasal congestion), chills, fatigue, weakness, sore throat, cough, shortness of breath, vomiting, diarrhea, pneumonia, bronchitis, and death.

In certain embodiments, the invention provides methods to decrease viral load in a subject, the methods comprising administering to the subject an effective amount of an antibody or fragment thereof of the invention that binds influenza A group 2 HA and blocks influenza virus binding and/or entry into the host cell.

In certain embodiments, the antibody or antigen-binding fragment thereof may be administered prophylactically or therapeutically to a subject having, or at risk of having, or pre-disposed to developing an influenza infection. The subjects at risk include, but are not limited to, an immunocompromised person, for example, a person who is immunocompromised because of autoimmune disease, or those persons receiving immunosuppressive therapy (for example, following organ transplant), or those persons afflicted with human immunodeficiency syndrome (HIV) or acquired immune deficiency syndrome (AIDS), certain forms of anemia that deplete or destroy white blood cells, those persons receiving radiation or chemotherapy, or those persons afflicted with an inflammatory disorder. Other subjects at risk for acquiring an influenza infection include an elderly adult (more than 65 years of age), children younger than 2 years of age, healthcare workers, and people with underlying medical conditions such as pulmonary infection, heart disease or diabetes. Also, any person who comes into physical contact or close physical proximity with an infected individual has an increased risk of developing an influenza virus infection. Moreover, a subject is at risk of contracting an influenza infection due to proximity to an outbreak of the disease, e.g. subject resides in a densely-populated city or in close proximity to subjects having confirmed or suspected infections of influenza virus, or choice of employment, e.g. hospital worker, pharmaceutical researcher, traveler to infected area, or frequent flier.

In certain embodiments, the antibody or antigen-binding fragment thereof of the invention is administered in combination with a second therapeutic agent to the subject in need thereof. The second therapeutic agent may be selected from the group consisting of an anti-inflammatory drug (such as corticosteroids, and non-steroidal anti-inflammatory drugs), an anti-infective drug, a different antibody to influenza HA, an antibody to a different influenza antigen (e.g. the neuraminidase), an anti-viral drug, a decongestant, an antihistamine, a vaccine for influenza, a dietary supplement such as anti-oxidants and any other drug or therapy known in the art useful for ameliorating at least one symptom of the influenza infection, or for reducing the viral load in a patient. In certain embodiments, the second therapeutic agent may be an agent that helps to counteract or reduce any possible side effect(s) associated with an antibody or antigen-binding fragment thereof of the invention, if such side effect(s) should occur. The antibody or fragment thereof may be administered subcutaneously, intravenously, intradermally, intraperitoneally, orally, intranasally, intramuscularly, or intracranially. In one embodiment, the antibody may be administered as a single intravenous infusion for maximum concentration of the antibody in the serum of the subject. The antibody or fragment thereof may be administered at a dose of about 0.01 mg/kg of body weight to about 100 mg/kg of body weight of the subject. In certain embodiments, an antibody of the present invention may be administered at one or more doses comprising between 50 mg to 5000 mg.

The present invention also includes use of an anti-influenza A group 2 HA antibody or antigen-binding fragment thereof of the invention for treating a disease or disorder that would benefit from the blockade of influenza HA binding and/or activity. The present invention also includes use of an anti-influenza A group 2 HA antibody or antigen-binding fragment thereof of the invention in the manufacture of a medicament for the treatment of a disease or disorder that would benefit from the blockade of influenza HA binding and/or activity.

Other embodiments will become apparent from a review of the ensuing detailed description.

BRIEF DESCRIPTION OF THE FIGURES

FIGS. 5A, 5B, 5C: Show that a single dose of anti-group 2 HA antibodies H1H14611N2 and H1H14612N2 demonstrate complete protection against a lethal influenza infection when administered as a single dose of 15 mg/kg at 24 (A), 48 (B) or 72 (C) hours after infection with 5×MLD$_{50}$ of A/Aichi/02/1968-PR8-X31 (H3N2).

DETAILED DESCRIPTION

Figure 1A:
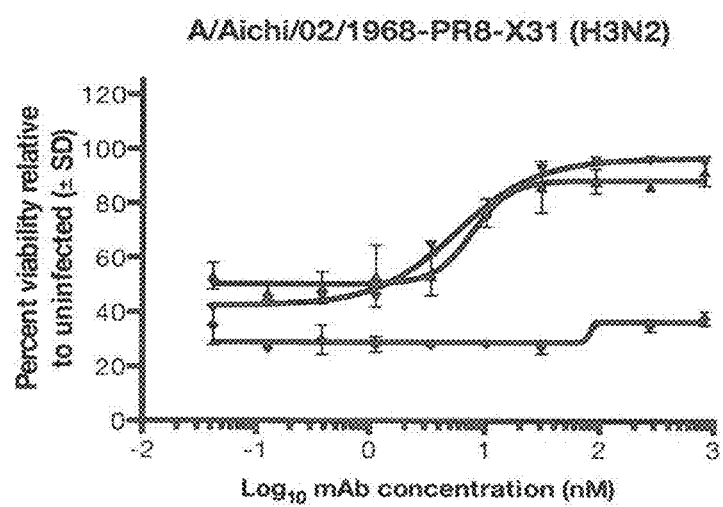
FIGS. 1A, 1B, 1C: Show that a single dose of H1H14611N2 and H1H14612N2 potently neutralizes three different strains of Group 2 Influenza A viruses in vitro. 1A: A/Aichi/02/1968-PR8-X31 (H3N2); 1B: A/Philippines/01/1982 (H3N2) and 1C: A/Shanghai/01/2013-PR8 (H7N9).
Figure 1B:
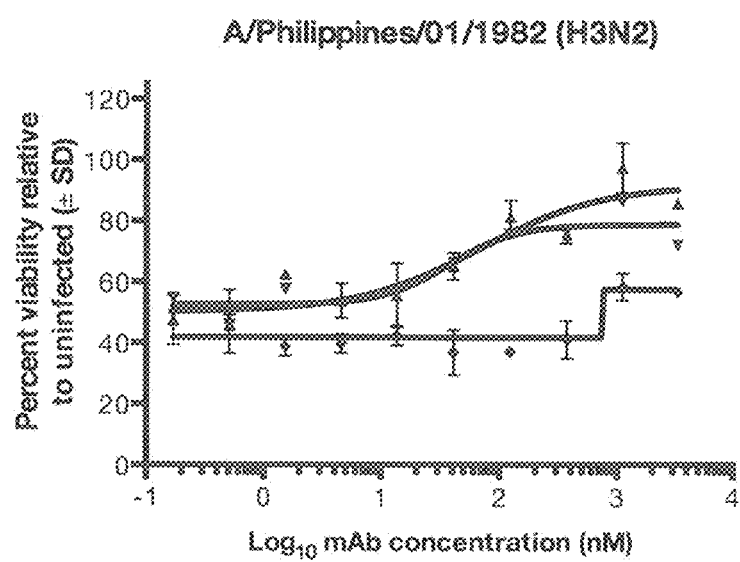
Figure 1C:
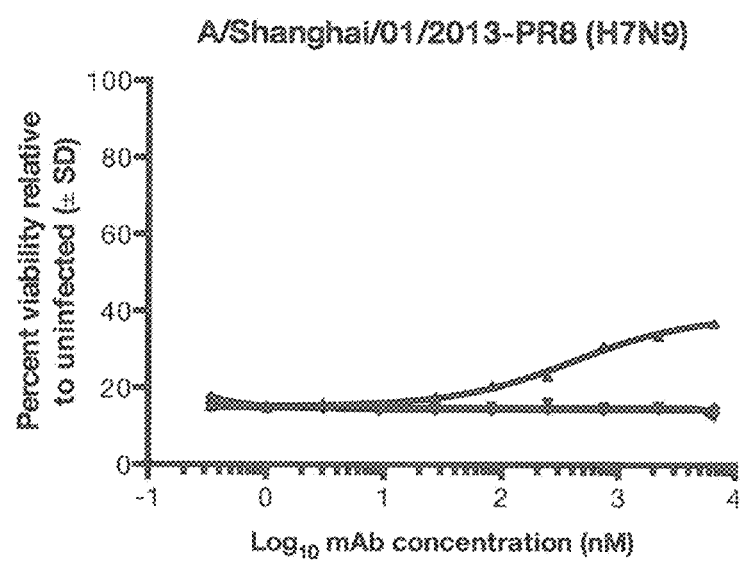
Figure 2:
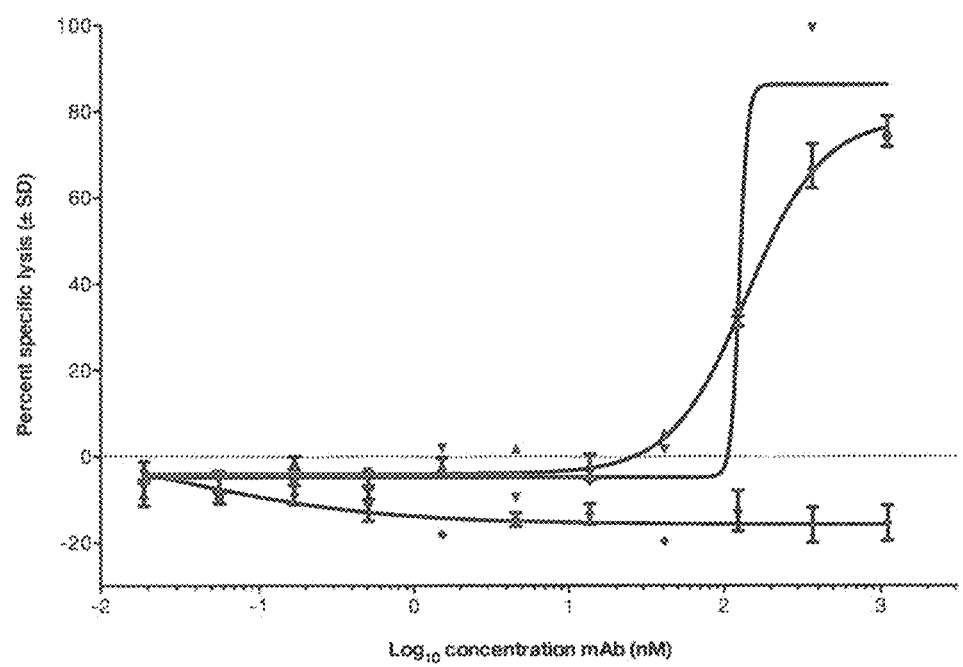
FIG. 2: Shows that H1H14611N2 and H1H14612N2 mediate complement-dependent cytotoxicity of A/Aichi/02/1968-PR8-X31 infected cells.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this

Definitions

The term "influenza hemagglutinin", also called "influenza HA" is a trimeric glycoprotein found on the surface of influenza virions, which mediates viral attachment (via HA1 binding to α-2,3- or α-2,6-sialic acids) and entry (through conformational change) into host cells. The HA is comprised of two structural domains: a globular head domain containing the receptor binding site (subject to high frequency of antigenic mutations) and the stem region (more conserved among various strains of influenza virus). The influenza HA is synthesized as a precursor (HA0) that undergoes proteolytic processing to produce two subunits (HA1 and HA2), which associate with one another to form the stem/globular head structure. The viral HA is the most variable antigen on the virus (18 subtypes can be classified into two groups), but the stem (HA2) is highly conserved within each group.

The amino acid sequence of full-length Influenza HA is exemplified by the amino acid sequence of influenza isolate H3N2A/Wisconsin/67/X-161/2005 provided in GenBank as accession number ACF41911.1 (Also shown here as SEQ ID NO: 33), or H7N7A/chicken/Netherlands/01/2003, accession number AAR02640.1(Also shown here as SEQ ID NO: 34). The term "influenza-HA" also includes protein variants of influenza HA isolated from different influenza isolates. The term "influenza-HA" also includes recombinant influenza HA or a fragment thereof. The term also encompasses influenza HA or a fragment thereof coupled to, for example, histidine tag, mouse or human Fc, or a signal sequence.

The term "influenza infection", as used herein, also characterized as "flu" refers to the severe acute respiratory illness caused by influenza virus. The term includes respiratory tract infection and the symptoms that include high fever, headache, general aches and pains, fatigue and weakness, in some instances extreme exhaustion, stuffy nose, sneezing, sore throat, chest discomfort, cough, shortness of breath, bronchitis, pneumonia and death in severe cases.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-influenza-HA monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired properties such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human anti-influenza-HA monoclonal antibodies comprising variants of any of the HCVR, LCVR, and/or CDR amino acid sequences disclosed herein having one or more conservative substitutions. For example, the present invention includes anti-influenza-HA antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "recombinant", as used herein, refers to antibodies or antigen-binding fragments thereof of the invention created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by real-time, label free bio-layer interferometry assay on an Octet® HTX biosensor, which bind specifically to influenza-HA. Moreover, multi-specific antibodies that bind to one domain in influenza-HA and one or more additional antigens or a bi-specific that binds to two different regions of influenza-HA are nonetheless considered antibodies that "specifically bind", as used herein.

The term "high affinity" antibody refers to those mAbs having a binding affinity to influenza-HA, expressed as $K_D$, of at least $10^{-8}$ M; preferably $10^{-9}$ M; more preferably $10^{-19}$M, even more preferably $10^{-11}$ M, even more preferably $10^{-12}$ M, as measured by real-time, label free bio-layer interferometry assay, e.g., an Octet® HTX biosensor, or by surface plasmon resonance, e.g., BIACORE™, or by solution-affinity ELISA.

By the term "slow off rate", "Koff" or "kd" is meant an antibody that dissociates from influenza-HA, with a rate constant of $1\times10^{-3}$ s$^{-1}$ or less, preferably $1\times10^{-4}$ s$^{-1}$ or less, as determined by real-time, label free bio-layer interferometry assay, e.g., an Octet® HTX biosensor, or by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to Influenza HA.

In specific embodiments, antibody or antibody fragments of the invention may be conjugated to a moiety such a ligand or a therapeutic moiety ("immunoconjugate"), such as an anti-viral drug, a second anti-influenza antibody, or any other therapeutic moiety useful for treating an infection caused by influenza virus.

An "isolated antibody", as used herein, is intended to refer to an antibody that is substantially free of other antibodies (Abs) having different antigenic specificities (e.g., an isolated antibody that specifically binds influenza-HA, or a fragment thereof, is substantially free of Abs that specifically bind antigens other than influenza-HA.

A "blocking antibody" or a "neutralizing antibody", as used herein (or an "antibody that neutralizes influenza-HA activity" or "antagonist antibody"), is intended to refer to an antibody whose binding to influenza-HA results in inhibition of at least one biological activity of influenza-HA. For example, an antibody of the invention may prevent or block influenza attachment to, or entry into a host cell. In addition, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used, alone or in combination, as prophylactic or therapeutic agents with other anti-viral agents upon appropriate formulation, or in association with active vaccination, or as a diagnostic tool.

The term "surface plasmon resonance", refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.

Bio-layer interferometry is a label-free technology for measuring biomolecular interactions. It is an optical analytical technique that analyzes the interference pattern of white light reflected from two surfaces: a layer of immobilized protein on the biosensor tip, and an internal reference layer. Any change in the number of molecules bound to the biosensor tip causes a shift in the interference pattern that can be measured in real-time (Abdiche, Y. N., et al. Analytical Biochemistry, (2008), 377(2), 209-217). In certain embodiments of the invention, a "real-time bio-layer interferometer based biosensor (Octet HTX assay)" was used to assess the binding characteristics of certain of the anti-influenza HA antibodies.

The term "$K_D$", as used herein, is intended to refer to the equilibrium dissociation constant of a particular antibody-antigen interaction.

The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "cross-competes", as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. To determine if a test antibody cross-competes with a reference anti-influenza A group 2 antibody of the invention, the reference antibody is allowed to bind to an influenza virus HA or peptide under saturating conditions. Next, the ability of a test antibody to bind to the influenza virus HA is assessed. If the test antibody is able to bind to influenza virus HA following saturation binding with the reference anti-influenza virus HA antibody, it can be concluded that the test antibody binds to a different epitope than the reference anti-influenza virus HA antibody. On the other hand, if the test antibody is not able to bind to the influenza virus HA following saturation binding with the reference anti-influenza virus HA antibody, then the test antibody may bind to the same epitope as the epitope bound by the reference anti-influenza virus HA antibody of the invention.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, more preferably a human, in need of amelioration, prevention and/or treatment of a disease or disorder such as viral infection. The subject may have an influenza infection or is predisposed to developing an influenza virus infection. Subjects "predisposed to developing an influenza virus infection", or subjects "who may be at elevated risk for contracting an influenza virus infection", are those subjects with compromised immune systems because of autoimmune disease, those persons receiving immunosuppressive therapy (for example, following organ transplant), those persons afflicted with human immunodeficiency syndrome (HIV) or acquired immune deficiency syndrome (AIDS), certain forms of anemia that deplete or destroy white blood cells, those persons receiving radiation or chemotherapy, or those persons afflicted with an inflammatory disorder. Additionally, subject of extreme young or old age are at increased risk. Any person who comes into physical contact or close physical proximity with an infected individual has an increased risk of developing an Influenza virus infection. Moreover, a subject is at risk of contracting an influenza infection due to proximity to an outbreak of the disease, e.g. subject resides in a densely-populated city or in close proximity to subjects having confirmed or suspected infections of Influenza virus, or choice of employment, e.g. hospital worker, pharmaceutical researcher, traveler to infected area, or frequent flier.

As used herein, the terms "treat", "treating", or "treatment" refer to the reduction or amelioration of the severity of at least one symptom or indication of influenza infection due to the administration of a therapeutic agent such as an antibody of the present invention to a subject in need thereof. The terms include inhibition of progression of disease or of worsening of infection. The terms also include positive prognosis of disease, i.e., the subject may be free of infection or may have reduced or no viral titers upon administration of a therapeutic agent such as an antibody of the present invention. The therapeutic agent may be administered at a therapeutic dose to the subject.

The terms "prevent", "preventing" or "prevention" refer to inhibition of manifestation of influenza infection or any symptoms or indications of influenza infection upon administration of an antibody of the present invention. The term includes prevention of spread of infection in a subject exposed to the virus or at risk of having influenza infection.

As used herein a "protective effect" may be demonstrated by any standard procedure known in the art to determine whether an agent such as an anti-viral agent, or an antibody such as an anti-influenza-HA antibody of the invention can demonstrate any one or more of the following: e.g. an increase in survival after exposure to an infectious agent, a decrease in viral load, or amelioration of at least one symptom associated with the infectious agent.

As used herein, the term "anti-viral drug" refers to any anti-infective drug or therapy used to treat, prevent, or ameliorate a viral infection in a subject. The term "anti-viral drug" includes, but is not limited to TAMIFLU® (Oseltamivir), RELENZA® (Zanamivir), ribavirin, or interferon-alpha2b. In the present invention, the infection to be treated is caused by an influenza virus.

General Description

Influenza is an infectious disease caused by RNA viruses of the family Orthomyxoviridae (the influenza viruses). Influenza viruses are classified based on core protein into three genera A, B and C that are further divided into subtypes determined by the viral envelope glycoproteins hemagginase (HA) and neuraminidase (NA). Influenza A viruses infect a range of mammalian and avian species, whereas type B and C infections are largely restricted to humans. Only types A and B cause human disease of any concern.

High mutation rates and frequent genetic reassortments of the influenza viruses contribute to great variability of the HA and NA antigens. Minor point mutations causing small changes ("antigenic drift") occur relatively often. Antigenic drift enables the virus to evade immune recognition, resulting in repeated influenza outbreaks during interpandemic years. Major changes in the HA antigen ("antigenic shift") are caused by reassortment of genetic material from different influenza A subtypes. Antigenic shifts resulting in new pandemic strains are rare events, occurring through reassortment between animal and human subtypes, for example in co-infected pigs.

The neutralizing antibody response to Influenza A virus is typically specific for a given viral subtype. There are 18 influenza A subtypes defined by their hemagglutinin ("HA") proteins. The 18 HAs, H1-H18, can be classified into two groups. Group 1 consists of H1, H2, H5, H6, H8, H9, H11, H12, H13, H16, H17 and H18 subtypes, and group 2 includes H3, H4, H7, H10, H14 and H15 subtypes. For these reasons it would be highly desirable to have a vaccine that induces broadly neutralizing antibodies capable of neutralizing all influenza A virus subtypes as well as their yearly variants. In addition broadly neutralizing heterosubtypic antibodies could be administered as medicaments for prevention or therapy of influenza A infection.

HA is synthesized as a homo-trimeric precursor polypeptide HA0. Each monomer can be independently cleaved post-translationally to form two polypeptides, HA1 and HA2, linked by a single disulphide bond. The larger N-terminal fragment (HAL 320-330 amino acids) forms a membrane-distal globular domain that contains the receptor-binding site and most determinants recognized by virus-neutralizing antibodies. The HA1 polypeptide of HA is responsible for the attachment of virus to the cell surface. The smaller C-terminal portion (HA2, approximately 180 amino acids) forms a stem-like structure that anchors the globular domain to the cellular or viral membrane. The HA2 polypeptide mediates the fusion of viral and cell membranes in endosomes, allowing the release of the ribonucleoprotein complex into the cytoplasm.

There has only been limited success in identifying antibodies that neutralize more than one subtype of influenza A virus. Further, the breath of neutralization of antibodies identified thus far is narrow and their potency is low. Okuno et al, immunized mice with influenza virus A/Okuda/57 (H2N2) and isolated a monoclonal antibody (C179) that binds to a conserved conformational epitope in HA2 and neutralizes the Group 1 H2, H1 and H5 subtype influenza A viruses in vitro and in vivo in animal models ((Okuno et al., J. Virol. 67:2552-8, 1993).

Despite decades of research, there are no marketed antibodies that broadly neutralize or inhibit influenza A virus infection or attenuate disease caused by influenza A virus. Therefore, there is a need to identify new antibodies that neutralize multiple subtypes of influenza A virus and can be used as medicaments for prevention or therapy of influenza A infection.

Passive immunotherapy for prophylaxis or treatment of infectious diseases has been used for more than a century, usually in the form of convalescent human sera that contains high titers of neutralizing antibodies (Good et al. 1991;

Cancer 68: 1415-1421). Today, multiple purified monoclonal antibodies are currently in preclinical and clinical development for use as anti-microbials (Marasco et al. 2007; Nature Biotechnology 25: 1421-1434).

The inventors have described herein fully human antibodies and antigen-binding fragments thereof that specifically bind to influenza hemagglutinin and modulate the interaction of influenza virus with host cells. The anti-influenza A group 2 HA antibodies may bind to the influenza virus HA with high affinity. In certain embodiments, the antibodies of the present invention are blocking antibodies wherein the antibodies may bind to influenza HA and block the attachment to and/or entry of the virus into host cells. In some embodiments, the blocking antibodies of the invention may block the binding of influenza virus to cells and as such may inhibit or neutralize viral infectivity of host cells. In some embodiments, the blocking antibodies may be useful for treating a subject suffering from an influenza virus infection. The antibodies when administered to a subject in need thereof may reduce the infection by a virus such as influenza in the subject. They may be used to decrease viral loads in a subject. They may be used alone or as adjunct therapy with other therapeutic moieties or modalities known in the art for treating a viral infection. In certain embodiments, these antibodies may bind to an epitope in the stem region of the viral HA. Furthermore, the identified antibodies can be used prophylactically (before infection) to protect a mammal from infection, or can be used therapeutically (after infection is established) to ameliorate a previously established infection, or to ameliorate at least one symptom associated with the infection.

The full-length amino acid sequences of two exemplary Influenza A group 2 HAs are shown in GenBank as accession numbers ACF41911.1 (from A/Wisconsin/67/X-161/2005 (H3N2), see also SEQ ID NO: 33) and accession number AAR02640.1 (from A/chicken/Netherlands/01/2003 (H7N7) (See also SEQ ID NO:34).

In certain embodiments, the antibodies of the invention are obtained from mice immunized with a primary immunogen, such as a full-length influenza HA or with a recombinant form of influenza HA or fragments thereof followed by immunization with a secondary immunogen, or with an immunogenically active fragment of influenza HA. In certain embodiments, the antibodies are obtained from mice immunized with an influenza vaccine composition followed by booster immunization with one or more recombinantly produced HA peptides.

In certain embodiments, the mice were immunized with A/Hong Kong/08/1968 (H3N2) followed by A/Hong Kong/05/1972-PR8-X36 (H3N2) and then again with A/Hong Kong/08/1968 (H3N2). All mice were boosted with a 1:1 mixture of DNAs encoding the HA from A/Wisconsin/67/X-161/2005 (H3N2) and A/chicken/Netherlands/01/2003 (H7N7).

The immunogen may be a biologically active and/or immunogenic fragment of influenza HA or DNA encoding the active fragment thereof. The fragment may be derived from the stem region of the HA protein. (See Sui et. al., Nature Struct. and Mol. Biol. Published online 22 Feb. 2009; Pages 1-9).

The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization.

Certain anti-influenza A group 2 HA antibodies of the present invention are able to bind to and neutralize the activity of influenza-HA, as determined by in vitro or in vivo assays. The ability of the antibodies of the invention to bind to and neutralize the activity of influenza A group 2 HA and thus the attachment and/or entry of the virus into a host cell followed by the ensuing viral infection, may be measured using any standard method known to those skilled in the art, including binding assays, or activity assays, as described herein.

Non-limiting, exemplary in vitro assays for measuring binding activity are illustrated in Example 3, herein. In Example 3, the binding affinity and dissociation constants of anti-influenza A group 2 HA antibodies for influenza A group 2 HA were determined by surface plasmon resonance using a Biacore instrument. In Example 4, neutralization assays were used to determine infectivity of diverse group 2 strains of influenza virus. In Example 5, certain antibodies were shown to mediate complement dependent cytotoxicity (CDC), or in Example 6, certain antibodies were shown to mediate antibody dependent cell-mediated cytotoxicity (ADCC) of virus-infected cells in vitro. Example 7 demonstrates that certain antibodies of the invention are capable of neutralizing an influenza A infection in vivo.

The antibodies specific for influenza A group 2 HA may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antibodies may be used in diagnostic assays including imaging assays.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to influenza A group 2 HA. An antibody fragment may include a Fab fragment, a F(ab')2 fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2, (v) $V_H$-$C_H$1-$C_H$2-$C_H$3; (vi) $V_H$-$C_H$2-$C_H$3; (vii) $V_H$-$C_L$; $V_L$—$C_H$1; (ix) $V_L$-$C_H$2; (X) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to Influenza A group 2 HA. An immunogen comprising any one of the following can be used to generate antibodies to influenza A group 2 HA. In certain embodiments, the antibodies of the invention are obtained from mice immunized with a full length, native influenza A group 2 HA (See, for example, GenBank accession numbers ACF41911.1, or AAR02640.1), or with a live attenuated or inactivated virus, or with DNA encoding the protein or fragment thereof. Alternatively, the influenza A group 2 HA protein or a fragment thereof may be produced using standard biochemical techniques and modified and used as immunogen. In one embodiment, the immunogen may be a recombinantly produced influenza A group 2 HA protein or fragment thereof. In certain embodiments of the invention, the immunogen may be an influenza virus vaccine. In certain embodiments, one or more booster injections may be administered. In certain embodiments, the booster injections may comprise one or more influenza virus strains, or hemagglutinins derived from these strains, eg., A/Hong Kong/08/1968 (H3N2) followed by A/Hong Kong/05/1972-PR8-X36 (H3N2) and then again with A/Hong Kong/08/1968 (H3N2). All mice were boosted with a 1:1 mixture of DNAs encoding the HA from A/Wisconsin/67/X-161/2005 (H3N2) and A/chicken/Netherlands/01/2003 (H7N7). In certain embodiments, the booster injections may contain a 1:1 mixture of the influenza strains, or a 1:1 mixture of the hemagglutinins derived from the strains, or the DNA encoding the HAs. In certain embodiments, the immunogen may be a recombinant influenza HA peptide expressed in *E. coli* or in any other eukaryotic or mammalian cells such as Chinese hamster ovary (CHO) cells or influenza virus itself.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to influenza A group 2 HA are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-influenza A group 2 HA antibodies and antibody fragments of the present invention encompass proteins having amino acid sequences that vary from those of the described antibodies, but that retain the ability to bind Influenza HA. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-influenza-HA Antibodies Comprising Fc Variants

According to certain embodiments of the present invention, anti-influenza A group 2 HA antibodies are provided comprising an Fc domain comprising one or more mutations, which enhance or diminish antibody binding to the FcRn receptor, e.g., at acidic pH as compared to neutral pH. For example, the present invention includes anti-influenza-HA antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-influenza A group 2 HA antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., I307A, E380A and N434A); and 433K and 434F (e.g., H433K and N434F). All possible combinations of the foregoing Fc domain mutations and other mutations within the antibody variable domains disclosed herein, are contemplated within the scope of the present invention.

The present invention also includes anti-influenza A group 2 HA antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_{H2}$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Provisional Appl. No. 61/759,578, filed Feb. 1, 2013, the disclosure of which is hereby incorporated by reference in its entirety).

Biological Characteristics of the Antibodies

In general, the antibodies of the present invention function by binding to Influenza A group 2 HA. For example, the present invention includes antibodies and antigen-binding fragments of antibodies that bind Influenza A group 2 HA (e.g., at 25° C. or at 37° C.) with a $K_D$ of less than 10 nM, as measured by surface plasmon resonance in a Biacore instrument, or by real-time bio-layer interferometer based biosensor (Octet HTX assay). In certain embodiments, the antibodies or antigen-binding fragments thereof bind influenza A group 2 HA with a $K_D$ of less than about 5 nM, less than about 2 nM, less than about 1 nM, less than about 500 pM, less than 250 pM, or less than 100 pM, as measured by surface plasmon resonance, e.g., using the assay format as described herein, or a substantially similar assay.

The present invention also includes antibodies and antigen-binding fragments thereof that bind Influenza A group 2 HA with a dissociative half-life (t½) of greater than about 75 minutes as measured by surface plasmon resonance at 37° C., e.g., using an assay format as defined herein, or a substantially similar assay. In certain embodiments, the antibodies or antigen-binding fragments of the present invention bind Influenza HA with a t½ of greater than about 200 minutes, greater than about 300 minutes, greater than about 400 minutes, greater than about 500 minutes, greater than about 600 minutes, greater than about 700 minutes, greater than about 800 minutes, greater than about 900 minutes, or greater than about 1000 minutes as measured by surface plasmon resonance at 25° C., e.g., using an assay format as defined herein (e.g., mAb-capture or antigen-capture format), or a substantially similar assay.

The present invention also includes antibodies or antigen-binding fragments thereof that neutralize the infectivity of influenza virus for its host cells. In some embodiments, the antibodies exhibit a neutralization potency against various representative group 2 influenza viruses A/Aichi/02/1968-PR8-X31 (H3N2); A/Philippines/01/1982 (H3N2) and A/Shanghai/01/2013-PR8 (H7N9) with an $IC_{50}$ ranging from about 5.7 nM to about 405 nM in a microneutralization assay, e.g., as shown in Example 4, or a substantially similar assay.

The present invention also includes antibodies or antigen-binding fragments thereof that mediate complement-dependent cytotoxicity of infected cells with an $EC_{50}$ of 140 nM with maximal lysis of 78.3% (See Example 5). In one embodiment, the antibodies or antigen-binding fragments thereof mediate antibody-dependent cell-mediated cytotoxicity (ADCC) of infected cells, as shown by a reporter assay and by the ability to lyse HA decorated cells using peripheral blood mononuclear cells (PBMC). In the reporter assay, the $EC_{50}$ was 0.8714 nM for H1H14611N2 and 0.6882 nM for H1H14612N2. In the PBMC type assay, the $EC_{50}$ was 0.1463 nM for H1H14611N2 and 0.1762 nM for H1H14612N2. (See Example 6).

The present invention also includes anti-influenza A group 2 HA antibodies that demonstrate an increase in protection, or potent neutralization of influenza A infection in vivo. Certain antibodies show potent neutralization when administered therapeutically (after infection; see Example 7). In one embodiment, one dose of H1H14611N2 at 7 mg/kg or 15 mg/kg administered at 96 hours post infection resulted in 80% and 100% survival of mice (respectively) when administered therapeutically. One hundred percent survival was also observed when certain exemplary antibodies (H1H14611N2 and H1H14612N2) were administered as a single dose of 15 mg/kg at 24, 48, or 72 hours after infection. In one embodiment, H1H14611N2 demonstrated an additive protective effect in influenza-infected mammals when combined with an anti-viral drug, oseltamivir.

In one embodiment, the invention provides an isolated recombinant antibody or antigen-binding fragment thereof that specifically binds to influenza A group 2 HA, wherein the antibody has two or more of the following characteristics: (a) is a fully human monoclonal antibody; (b) binds to influenza A group 2 HA with a dissociation constant ($K_D$) of less than $10^{-8}$ M, as Measured by Surface Plasmon Resonance; (c) Demonstrates a Dissociative Half-Life (t½) Greater than 75 minutes;
(d) demonstrates neutralization of influenza A group 2 viruses selected from H3N2 and H7N9 strains with an $IC_{50}$ of less than 200 nM and 500 nM, respectively; (e) demonstrates complement mediated lysis of influenza virus infected cells with an $EC_{50}$ of less than about 150 nM; (f) demonstrates antibody-dependent cell-mediated cytotoxicity of virus infected target cells using a reporter bioassay with an $EC_{50}$ of less than about 0.9 nM; (g) demonstrates antibody-dependent cell-mediated cytotoxicity of virus infected target cells in the presence of human peripheral blood mononuclear cells (PBMC) with an $EC_{50}$ of less than about 0.180 nM; (h) demonstrates an increase in survival in an influenza-infected animal when administered at 24, 48, 72, or 96 hours after virus challenge; (i) demonstrates an increase in survival in an influenza-infected animal when administered in combination with oseltamivir at 96 hours after infection; or (j) wherein the antibody or antigen-binding fragment thereof comprises three heavy chain complementarity determining regions (CDRs) (HCDR1, HCDR2 and HCDR3) contained within any one of the heavy chain variable region (HCVR) sequences listed in Table 1; and three light chain CDRs (LCDR1, LCDR2 and LCDR3) contained within any one of the light chain variable region (LCVR) sequences listed in Table 1.

The antibodies of the present invention may possess two or more of the aforementioned biological characteristics, or any combinations thereof. Other biological characteristics of the antibodies of the present invention will be evident to a person of ordinary skill in the art from a review of the present disclosure including the working Examples herein.

Epitope Mapping and Related Technologies

The present invention includes anti-influenza A group 2 HA antibodies, which interact with one or more amino acids found within one or more domains of the influenza A group 2 HA molecule. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within the influenza HA molecule (e.g. a linear epitope in a domain). Alternatively, the epitope may consist of a plurality of non-contiguous amino acids (or amino acid sequences) located within the influenza A group 2 HA molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the influenza virus A group 2 HA antibodies or antigen-binding fragments thereof bind an epitope within any one or more of the regions exemplified in influenza HA, either in natural form, or recombinantly produced, or to a fragment thereof.

The present invention includes anti-influenza A group 2 HA antibodies that bind to the same epitope, or a portion of the epitope. Likewise, the present invention also includes anti-influenza A group 2 HA antibodies that compete for binding to influenza A group 2 HA or a fragment thereof with any of the specific exemplary antibodies described herein. For example, the present invention includes anti-influenza A group 2 HA antibodies that cross-compete for binding to influenza A group 2 HA with one or more antibodies obtained from those antibodies described in Table 1.

One can easily determine whether an antibody binds to the same epitope as, or competes for binding with, a reference anti-influenza A group 2 HA antibody by using routine methods known in the art. For example, to determine if a test antibody binds to the same epitope as a reference anti-influenza A group 2 HA antibody of the invention, the reference antibody is allowed to bind to an influenza A group 2 HA or peptide under saturating conditions. Next, the ability of a test antibody to bind to the influenza A group 2 HA molecule is assessed. If the test antibody is able to bind to influenza A group 2 HA following saturation binding with the reference anti-influenza A group 2 HA antibody, it can be concluded that the test antibody binds to a different epitope than the reference anti-influenza A group 2 HA antibody. On the other hand, if the test antibody is not able to bind to the influenza A group 2 HA following saturation binding with the reference anti-influenza A group 2 HA antibody, then the test antibody may bind to the same epitope as the epitope bound by the reference anti-influenza A group 2 HA antibody of the invention.

To determine if an antibody competes for binding with a reference anti-influenza A group 2 HA antibody, the above-described binding methodology is performed in two orientations: In a first orientation, the reference antibody is allowed to bind to an influenza A group 2 HA under saturating conditions followed by assessment of binding of the test antibody to the influenza A group 2 HA molecule. In a second orientation, the test antibody is allowed to bind to an influenza A group 2 HA molecule under saturating conditions followed by assessment of binding of the reference antibody to the influenza A group 2 HA molecule. If, in both orientations, only the first (saturating) antibody is capable of binding to the influenza A group 2 HA molecule, then it is concluded that the test antibody and the reference antibody compete for binding to influenza A group 2 HA. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res.

1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-influenza A group 2 HA monoclonal antibody conjugated to a therapeutic moiety ("immunoconjugate"), such as a toxoid or an anti-viral drug to treat influenza virus infection. As used herein, the term "immunoconjugate" refers to an antibody, which is chemically or biologically linked to a radioactive agent, a cytokine, an interferon, a target or reporter moiety, an enzyme, a peptide or protein or a therapeutic agent. The antibody may be linked to the radioactive agent, cytokine, interferon, target or reporter moiety, enzyme, peptide or therapeutic agent at any location along the molecule so long as it is able to bind its target. Examples of immunoconjugates include antibody drug conjugates and antibody-toxin fusion proteins. In one embodiment, the agent may be a second different antibody to Influenza-HA. In certain embodiments, the antibody may be conjugated to an agent specific for a virally infected cell. The type of therapeutic moiety that may be conjugated to the anti-influenza-HA antibody and will take into account the condition to be treated and the desired therapeutic effect to be achieved. Examples of suitable agents for forming immunoconjugates are known in the art; see for example, WO 05/103081.

Multi-Specific Antibodies

The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

Any of the multi-specific antigen-binding molecules of the invention, or variants thereof, may be constructed using standard molecular biological techniques (e.g., recombinant DNA and protein expression technology), as will be known to a person of ordinary skill in the art.

In some embodiments, influenza A group 2 HA-specific antibodies are generated in a bi-specific format (a "bi-specific") in which variable regions binding to distinct domains of influenza A group 2 HA are linked together to confer dual-domain specificity within a single binding molecule. Appropriately designed bi-specifics may enhance overall influenza A group 2 HA-protein inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind more than one domain and a second target, such as, but not limited to, for example, a second different anti-influenza A group 2 HA antibody, may be prepared in a bi-specific format using techniques described herein, or other techniques known to those skilled in the art. Antibody variable regions binding to distinct regions may be linked together with variable regions that bind to relevant sites on, for example, the influenza virus, to confer dual-antigen specificity within a single binding molecule. Appropriately designed bi-specifics of this nature serve a dual function. Variable regions with specificity for the extracellular domain are combined with a variable region with specificity for outside the extracellular domain and are paired on a structural scaffold that allows each variable region to bind to the separate antigens.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Administration and Formulations

The invention provides therapeutic compositions comprising the anti-influenza A group 2 HA antibodies or antigen-binding fragments thereof of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody of the present invention is used for treating a disease or disorder in an adult patient, or for preventing such a disease, it is advantageous to administer the antibody of the present invention normally at a single dose of about 0.1 to about 60 mg/kg body weight, more preferably about 5 to about 60, about 10 to about 50, or about 20 to about 50 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 5000 mg, about 1 to about 2000 mg, about 5 to about 1000 mg, or about 10 to about 500 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249:1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles may be developed and conjugated to antibodies contained in pharmaceutical compositions to target virally infected cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 5000 mg per dosage form in a unit dose; especially in the form of injection, it is preferred that the antibody is contained in about 5 to about 500 mg and in about 10 to about 250 mg for the other dosage forms.

Therapeutic Uses of the Antibodies

The antibodies of the present invention are useful for the treatment, and/or prevention of a disease or disorder or condition associated with influenza virus infection and/or for ameliorating at least one symptom associated with such disease, disorder or condition.

In certain embodiments, the antibodies of the invention are useful to treat subjects suffering from the severe and acute respiratory infection caused by influenza virus. In some embodiments, the antibodies of the invention are useful in decreasing viral titers or reducing viral load in the host. In one embodiment, an antibody or antigen-binding fragment thereof the invention may be administered at a therapeutic dose to a patient with influenza virus infection.

One or more antibodies of the present invention may be administered to relieve or prevent or decrease the severity of one or more of the symptoms or conditions of the disease or disorder. The antibodies may be used to ameliorate or reduce the severity of at least one symptom of influenza virus infection including, but not limited to fever, cough, sore throat, headache, body aches, fatigue, extreme exhaustion, shortness of breath, bronchitis, pneumonia, and death.

It is also contemplated herein to use one or more antibodies of the present invention prophylactically to subjects at risk for developing an influenza virus infection such as immunocompromised individuals, elderly adults (more than 65 years of age), children younger than 2 years of age, healthcare workers, family members in close proximity to a patient suffering from an influenza virus infection, and patients with a medical history (e.g., increased risk of pulmonary infection, heart disease or diabetes).

In a further embodiment of the invention the present antibodies are used for the preparation of a pharmaceutical composition for treating patients suffering from an influenza virus infection. In another embodiment of the invention, the present antibodies are used as adjunct therapy with any other agent or any other therapy known to those skilled in the art useful for treating or ameliorating an influenza virus infection.

Combination Therapies

Combination therapies may include an anti-influenza A group 2 HA antibody of the invention and any additional therapeutic agent that may be advantageously combined with an antibody of the invention, or with a biologically active fragment of an antibody of the invention. The antibodies of the present invention may be combined synergistically with one or more drugs or agents (e.g. anti-viral agents) used to treat influenza virus.

For example, exemplary anti-viral agents include, e.g., vaccines, neuraminidase inhibitors or nucleoside analogs. Other exemplary anti-viral agents that may be used in combination with an antibody of the invention can include, e.g., zidovudine, gangcyclovir, vidarabine, idoxuridine, trifluridine, foscarnet, acyclovir, ribavirin, amantadine, remantidine, saquinavir, indinavir, ritonavir, alpha-interferons and other interferons, a neuraminidase inhibitor (e.g., zanamivir (RELENZA®), oseltamivir (TAMIFLU®) laninamivir, peramivir), or rimantadine.

Other exemplary anti-viral drugs include, but are not limited to, a HA inhibitor, a sialic acid inhibitor and an M2 ion channel inhibitor. In one embodiment, the M2 ion channel inhibitor is amantadine or rimantadine.

In some embodiments, the antibodies of the invention may be combined with a second therapeutic agent to reduce the viral load in a patient with an influenza virus infection, or to ameliorate one or more symptoms of the infection.

The antibodies of the present invention may be used in combination with an anti-inflammatory drug (e.g., corticosteroids, and non-steroidal anti-inflammatory drugs), a decongestant, an anti-histamine, an anti-infective drug, a different antibody to Influenza virus, an anti-viral drug, a vaccine for influenza virus, such as FLUMIST® or FLUVIRIN®, a dietary supplement such as anti-oxidants or any other palliative therapy to treat an influenza virus infection.

In certain embodiments, the second therapeutic agent is another antibody to influenza. In certain embodiments, the second therapeutic agent is another antibody to influenza hemagglutinin. In certain embodiments, the second therapeutic agent is another antibody to a different influenza protein, such as the neuraminidase, or the tetrameric ectodomain of matrix protein 2 (M2e protein). In certain embodiments, the second therapeutic agent is an antibody to a different protein such as the host transmembrane protease, serine 2 (TMPRSS2). The second antibody may be specific for one or more different influenza virus proteins from different subtypes or strains of the virus. It is contemplated herein to use a combination ("cocktail") of antibodies with broad neutralization or inhibitory activity against influenza virus. In some embodiments, non-competing antibodies may be combined and administered to a subject in need thereof, to reduce the ability of influenza virus to escape due to rapid mutation as a result of selection pressure. In some embodiments, the antibodies comprising the combination bind to distinct non-overlapping epitopes on the HA protein. The antibodies comprising the combination may block the virus attachment and/or entry into and/or fusion with host cells. The antibodies may interact with a hemagglutinin selected from any one or more of the Group 2 influenza A subtypes including H3, H4, H7, H10, H14 and H15 subtypes and when used alone, or in combination with any one or more of the agents noted above, may neutralize any one or more of the Group 2 influenza subtypes including, but not limited to the following: H3N2, H7N9.

It is also contemplated herein to use a combination of anti-influenza A group 2 HA antibodies of the present invention, wherein the combination comprises one or more antibodies that do not cross-compete; In some embodiments, the combination includes a first antibody with broad neutralization activity with a second antibody with activity against a narrow spectrum of isolates and that does not cross-compete with the first antibody.

As used herein, the term "in combination with" means that additional therapeutically active component(s) may be administered prior to, concurrent with, or after the administration of the anti-influenza A group 2 HA antibody of the present invention. The term "in combination with" also includes sequential or concomitant administration of an anti-influenza-HA antibody and a second therapeutic agent.

The additional therapeutically active component(s) may be administered to a subject prior to administration of an anti-influenza A group 2 HA antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-influenza A group 2 HA antibody of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-influenza A group 2 HA antibody of the present invention. "Concurrent" administration, for purposes of the present invention, includes, e.g., administration of an anti-influenza A group 2 HA antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-influenza A group 2 HA antibody and the additional therapeutically active component may be administered intravenously, etc.); alternatively, each dosage form may be administered via a different route (e.g., the anti-influenza A group 2 HA antibody may be administered intravenously, and the additional therapeutically active component may be administered orally). In any event, administering the components in a single dosage from, in separate dosage forms by the same route, or in separate dosage forms by different routes are all considered "concurrent administration," for purposes of the present disclosure. For purposes of the present disclosure, administration of an anti-influenza A group 2 HA antibody "prior to", "concurrent with," or "after" (as those terms are defined herein above) administration of an additional therapeutically active component is considered administration of an anti-influenza A group 2 HA antibody "in combination with" an additional therapeutically active component.

The present invention includes pharmaceutical compositions in which an anti-influenza A group 2 HA antibody of the present invention is co-formulated with one or more of the additional therapeutically active component(s) as described elsewhere herein.

Administration Regimens

According to certain embodiments, a single dose of an anti-influenza A group 2 HA antibody of the invention (or a pharmaceutical composition comprising a combination of an anti-influenza A group 2 HA antibody and any of the additional therapeutically active agents mentioned herein) may be administered to a subject in need thereof. According to certain embodiments of the present invention, multiple doses of an anti-influenza A group 2 HA antibody (or a pharmaceutical composition comprising a combination of an anti-influenza A group 2 HA antibody and any of the additional therapeutically active agents mentioned herein) may be administered to a subject over a defined time course. The methods according to this aspect of the invention comprise sequentially administering to a subject multiple doses of an anti-influenza A group 2 HA antibody of the invention. As used herein, "sequentially administering" means that each dose of anti-influenza A group 2 HA antibody is administered to the subject at a different point in time, e.g., on different days separated by a predetermined interval (e.g., hours, days, weeks or months). The present invention includes methods which comprise sequentially administering to the patient a single initial dose of an anti-influenza A group 2 HA antibody, followed by one or more secondary doses of the anti-influenza A group 2 HA antibody, and optionally followed by one or more tertiary doses of the anti-influenza A group 2 HA antibody.

The terms "initial dose," "secondary doses," and "tertiary doses," refer to the temporal sequence of administration of the anti-influenza A group 2 HA antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-influenza-HA antibody, but generally may differ from one another in terms of frequency of administration. In certain embodiments, however, the amount of anti-influenza A group 2 HA antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 48 hours (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) after the immediately preceding dose. The phrase "the immediately preceding dose," as used herein, means, in a sequence of multiple administrations, the dose of anti-influenza A group 2 HA antibody, which is administered to a patient prior to the administration of the very next dose in the sequence with no intervening doses.

The methods according to this aspect of the invention may comprise administering to a patient any number of secondary and/or tertiary doses of an anti-influenza A group 2 HA antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-influenza A group 2 HA antibodies of the present invention may be used to detect and/or measure influenza A group 2 HA in a sample, e.g., for diagnostic purposes. Some embodiments contemplate the use of one or more antibodies of the present invention in assays to detect a disease or disorder such as viral infection. Exemplary diagnostic assays for influenza A group 2 HA may comprise, e.g., contacting a sample, obtained from a patient, with an anti-influenza A group 2 HA antibody of the invention, wherein the anti-influenza A group 2 HA antibody is labeled with a detectable label or reporter molecule or used as a capture ligand to selectively isolate influenza A group 2 HA from patient samples. Alternatively, an unlabeled anti-influenza A group 2 HA antibody can be used in diagnostic applications in combination with a secondary antibody which is itself detectably labeled. The detectable label or reporter molecule can be a radioisotope, such as $^3H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure influenza A group 2 HA in a sample include enzyme-linked immunosorbent assay (ELISA), radioimmunoassay (RIA), and fluorescence-activated cell sorting (FACS).

Samples that can be used in influenza A group 2 HA diagnostic assays according to the present invention include any tissue or fluid sample obtainable from a patient, which contains detectable quantities of either influenza A group 2 HA, or fragments thereof, under normal or pathological conditions. Generally, levels of influenza A group 2 HA in a particular sample obtained from a healthy patient (e.g., a patient not afflicted with a disease associated with influenza will be measured to initially establish a baseline, or standard, level of influenza A group 2 HA. This baseline level of influenza A group 2 HA can then be compared against the levels of influenza A group 2 HA measured in samples obtained from individuals suspected of having an influenza A group 2 HA-associated condition, or symptoms associated with such condition.

The antibodies specific for influenza A group 2 HA may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to Influenza A Group 2 Hemagglutinin (HA)

Human antibodies to influenza A group 2 HA were generated in a VELOCIMMUNE® mouse comprising DNA encoding human immunoglobulin heavy and kappa light chain variable regions. The mice were immunized with A/Hong Kong/08/1968 (H3N2) followed by A/Hong Kong/05/1972-PR8-X36 (H3N2) and then again with A/Hong Kong/08/1968 (H3N2). All mice were boosted with a 1:1 mixture of DNAs encoding the HA from A/Wisconsin/67/X-161/2005 (H3N2) and A/chicken/Netherlands/01/2003 (H7N7). The antibody immune response was monitored by an influenza A group 2 HA specific immunoassay. When a desired immune response was achieved, splenocytes were harvested and fused with mouse myeloma cells to preserve their viability and form hybridoma cell lines. The hybridoma cell lines were screened and selected to identify cell lines that produce influenza A group 2 HA-specific antibodies. Using this technique, and the various immunogens described above, several chimeric antibodies (i.e., antibodies possessing human variable domains and mouse constant domains) were obtained.

Anti-influenza A group 2 HA antibodies were also isolated directly from antigen-positive mouse B cells without fusion to myeloma cells, as described in U.S. Pat. No. 7,582,298, herein specifically incorporated by reference in its entirety. Using this method, several fully human anti-influenza HA antibodies (i.e., antibodies possessing human variable domains and human constant domains) were obtained.

Two exemplary antibodies described herein are designated H1H14611N2 and H1H14612N2.

The biological properties of the exemplary antibodies generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions and CDRs of selected anti-influenza A group 2 HA antibodies of the invention. The corresponding nucleic acid sequence identifiers are set forth in Table 2.

TABLE 1

| | Amino Acid Sequence Identifiers | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1H14611N2 | 2 | 4 | 6 | 8 | 10 | 12 | 14 | 16 |
| H1H14612N2 | 18 | 20 | 22 | 24 | 26 | 28 | 30 | 32 |

TABLE 2

| | Nucleic Acid Sequence Identifiers | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1H14611N2 | 1 | 3 | 5 | 7 | 9 | 11 | 13 | 15 |
| H1H14612N2 | 17 | 19 | 21 | 23 | 25 | 27 | 29 | 31 |

Antibodies are typically referred to herein according to the following nomenclature: Fc prefix (e.g. "H1H," "H2M," etc.), followed by a numerical identifier (e.g. "14611," "14612," etc., as shown in Table 1 or 2), followed by a "P," "P2," "N", N2, or "B" suffix. Thus, according to this nomenclature, an antibody may be referred to herein as, e.g., "H1H14611N2," "H1H14612N2," etc. The H1H or H2M prefixes on the antibody designations used herein indicate the particular Fc region isotype of the antibody. For example, an "H1 M" antibody has a mouse IgG1 Fc, and an "H2M" antibody has a mouse IgG2 Fc (a or b isotype) (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Tables 1 and 2 will remain the same, and the binding properties to antigen are expected to be identical or substantially similar regardless of the nature of the Fc domain.

Example 3: Binding Affinities and Kinetic Constants of Monoclonal Anti-Influenza A Group 2 HA Antibodies Binding affinities and kinetic constants of human monoclonal anti-influenza A group 2 HA antibodies were deter mined by surface plasmon resonance using an antigen-capture format. Measurements were conducted on a Biacore instrument. In this format, the Biacore high-density sensor surface was derivatized by amine coupling with a monoclonal mouse anti-human Fc antibody to capture anti-influenza A group 2 HA antibodies expressed with human Fc constant regions. Association of all the HA proteins to each of the captured mAbs was monitored using standard methods. The foldon proteins utilized in this experiment were obtained from BEI Resources or Influenza Reagent Resource (IRR), as shown below in Table 3. Binding dissociation, equilibrium constants ($K_D$) and dissociative half-lives (t½) were calculated from the kinetic rate constants as:

$$K_D(M) = \frac{ka}{kd},$$

and $$t\frac{1}{2}(\text{min}) = \frac{\ln(2)}{60 \times kd}$$

Binding kinetic parameters for HA proteins to the surface-bound anti-HA antibodies at 37° C. are summarized in Table 3.

TABLE 3

Binding Affinity and Kinetic parameters of H1H14611N2 binding to HA Foldon Proteins at 37° C.

| | Group 1 | | | | | | | | | | | | Group 2 | | | |
|---|---|---|---|---|---|---|---|---|---|---|---|---|---|---|---|---|
| | A/Brisbane/59/2007 (H1) BEI Resources (NR-28607) | | A/California/04/2009 (H1) BEI Resources (NR-15749) | | A/Puerto Rico/08/1934 (H1) BEI Resources (NR-19240) | | A/Vietnam/1203/2004 (H5) IRR (FR-39) | | A/Indonesia/05/2005 (H5) IRR (FR-59) | | A/Turkey/Wisconsin/01/1966 (H9) BEI Resources (NR-43782) | | A/Hiroshima/52/2005 (H3) IRR (FR-63) | | A/Shanghai/01/2013 (H7) BEI Resources (NR-44365) | |
| mAb | $K_D$ mol/l | $t_{1/2}$ min | $K_D$ mol/l | $t_{1/2}$ min | $K_D$ mol/l | $t_{1/2}$ min | $K_D$ mol/l | $t_{1/2}$ min | $K_D$ mol/l | $t_{1/2}$ min | $K_D$ mol/l | $t_{1/2}$ min | $K_D$ mol/l | $t_{1/2}$ min | $K_D$ mol/l | $t_{1/2}$ min |
| H1H14611N2 (Group 2 specificity) | NB | NB | NB | NB | NB | NB | NB | NB | NB | NB | NB | NB | 8.22E−09 | 86 | IC[§] | IC |
| Buffer | NB | NB | NB | NB | NB | NB | NB | NB | NB | NB | NB | NB | NB | NB | NB | NB |

IC[§]: Inconclusive

NB: Non-binding

Results

H1H14611N2 binds group 2, H3 HA with high affinity (Table 3). The equilibrium dissociation constant ($K_D$ value) was in the low nM range for A/Hiroshima/52/2005 (H3N2; $K_D$=8.22E$^{-09}$). H1H14611N2 did not bind to group 1 strains.

Example 4: H1H14611N2 and H1H14612N2 Potently Neutralize a Broad Range of Group 2 Influenza A Viruses The exemplary monoclonal antibodies (mAb) H1H14611N2 and H1H14612N2 were selected for in vitro microneutralization assays using two different formats to evaluate the breadth and potency of the antibodies.

Cell Viability Microneutralization Assay

Monoclonal antibodies were tested in a microneutralization assay to evaluate breadth and potency. In brief, Madin-Darby canine kidney (MDCK) cells were plated at $6.0\times10^3$ cells/well in a 96-well plate. Virus diluent only was added to background control wells. Cells were incubated for 4 to 5 hours at 37° C. with 5% $CO_2$. Monoclonal antibodies were diluted at 4 times final concentration in virus diluent. The antibodies were diluted 1:3 in duplicate. Virus was thawed on ice and diluted to the appropriate pre-determined concentration. Diluted virus was added to diluted mAbs. The mAb-virus mixture was immediately transferred to the MDCK cells and incubated at 37° C. with 5% $CO_2$ for 72 h. Virus control and uninfected cell control wells were also included. On day 4, the plates were centrifuged at 1200 RPM for 3 minutes. Cell were lysed using 100 μL CelTiter-Glo substrate and ATP release measured using luminescence (victor X3, PerkinElmer). Percent viability was determined relative to uninfected control. Viability values were analyzed using non-linear 4PL regression to determine $IC_{50}$ values (GraphPad Prism).

HA Microneutralization Assay

Briefly, Madin-Darby Canine Kidney (MDCK) cells were plated and incubated overnight to achieve 80-100% confluency the next day. Monoclonal antibodies were diluted in viral infection medium (VIM) to 50 μg/mL and diluted 1:2 in triplicate or quadruplicate. H5N1 A/Vietnam/1203/2004 or H1N1 A/California/07/2009 was diluted in VIM and added to the diluted antibodies and incubated for 1 h. The samples were then transferred to the MDCKs and incubated for 48 h. After the incubation, 50 μL of the supernatant was transferred to a new 96-well plate. Diluted turkey or horse red blood cells were added to the supernatant and incubated at room temperature for 30 or 60 min. The hemagglutination titer was recorded as the reciprocal of the last dilution that completely inhibited hemagglutination.

Results

The results showed that H1H14611N2 and H1H14612N2 neutralized numerous, diverse group 2 influenza A virus isolates in the microneutralization assays. The $IC_{50}$ (nM) for H1H14611N2 and H1H14612N2 with respect to the neutralization of three different strains of influenza (A/Aichi/02/1968-PR8-X31(H3N2), A/Philippines/01/1982 (H3N2) and A/Shanghai/01/2013-PR8 (H7N9)) are shown in Table 4 and the dose-response curves for the strains including A/Aichi/02/1968-PR8-X31 (H3N2), A/Phillipines/02/1982 (H3N2) and A/Shanghai/01/2013 (H7N9) are also shown in FIGS. 1 A, B and C, respectively (H1H14611N2 shown as triangles; H1H14612N2 shown as inverse triangles; irrelevant hIgG1 shown as diamonds). The results of additional neutralization studies against influenza strain A/Victoria/316/2011 (H3N2) using a hemagglutination readout are shown in Table 5. Shown in table 5 is the lowest concentration of mAb (nM) where no RBC hemagglutination was detected. Also included in these studies was a negative hIgG1 control.

TABLE 4

Summary of Neutralization Activity of Anti-group 2 HA mAbs against several Influenza Strains ($IC_{50}$ nM)

| mAb | A/Aichi/02/1968-PR8-X31 (H3N2) | A/Philippines/01/1982 (H3N2) | A/Shanghai/01/2013-PR8 (H7N9) |
|---|---|---|---|
| H1H14611N2 | 7.830 | 68.37 | 404.7 |
| H1H14612N2 | 5.700 | 37.60 | >6666 |
| Irrelevant/negative hIgG1 control | >833 | >3333 | >6666 |

Data are from one of at least three studies showing similar results.

TABLE 5

Summary of Neutralization Activity of Anti-group 2 HA mAbs against Influenza Strain A/Victoria/316/2011 (H3N2)

| mAb | Concentration (nM) |
|---|---|
| H1H14611N2 | 41.7 |
| H1H14612N2 | 166.7 |

Example 5. H1H14611N2 and H1H14612N2 Mediate Killing of Group 2 HA Virus-Infected Cells Via Complement-Dependent Cytotoxicity (CDC)

The exemplary monoclonal antibodies (mAb) H1H14611N2 and H1H14612N2 were selected for in vitro complement-dependent cytotoxicity (CDC) assays. Briefly, Madin-Darby Canine Kidney (MDCK) cells were infected with A/Aichi/02/1968-PR8-X31 (H3N2) at a multiplicity of infection (MOI) of 3, 30 hours prior to the assay. Target cells were combined with the indicated mAbs at the indicated concentrations. Normal human serum complement (NHSC) was prepared at three times the final concentration (15%) in CDC assay medium. Percent cytotoxicity was measured using CytoTox-Glo (Promega). Detergent lysed and serum background controls were used to determine maximum and background lysis values. Shown in FIG. 2 are H1H14611N2 (triangles), H1H14612N2 (inverse triangles), along with an irrelevant hIgG1 (diamonds) as a control. The percent specific lysis was calculated as ((lysis by mAb+NHSC)−(lysis by NHSC only))/((detergent maximal lysis)−(lysis by NHSC only))×100.

Results

H1H14611N2 and H1H14612N2 displayed a dose-dependent increase in capacity to specifically lyse virus-infected cells when tested in a CDC assay with A/Aichi/02/1968-PR8-X31(H3N2)-infected MDCKs in the presence of complement-preserved human serum. The results of one representative CDC assay of three are shown in FIG. 2. An irrelevant/negative hIgG1 control was also used in this experiment. H1H14611N2 and H1H14612N2 were effective at mediating cytolysis with a maximum lysis of 78.3% and 86.3% and $EC_{50}$s of 140 nM and 126 nM, respectively.

Example 6: H1H14611N2 and H1H14612N2 Potently Kill Group 2 HA-Expressing Cells Via Antibody-Dependent Cell-Mediated Cytotoxicity (ADCC)

The exemplary monoclonal antibodies H1H14611N2 and H1H14612N2 were selected for testing their ability to specifically lyse HA-decorated cells in two antibody-dependent cell-mediated cytotoxicity assays.

A. FcγRIIIA Activation Assay

Figure 3:
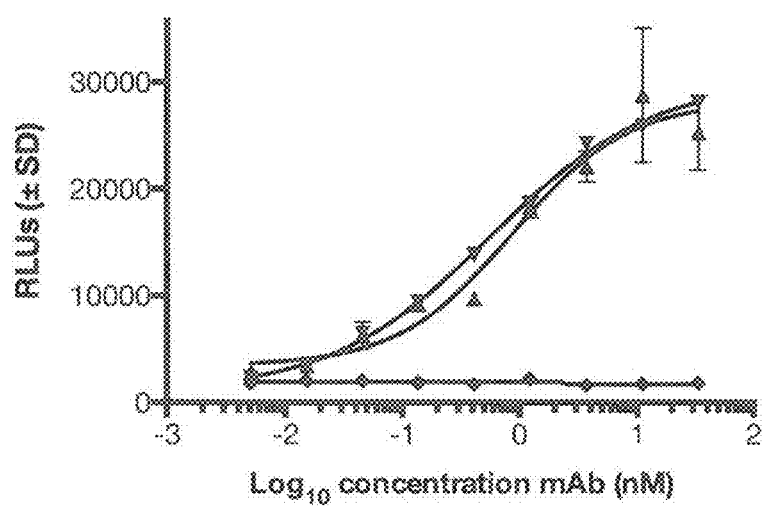
FIG. 3: Shows a dose response curve of anti-group 2 HA antibodies H1H14611N2 and H1H14612N2 in an FcγRIIIA activation assay.

An FcγRIIIA activation assay using the ADCC-Glo reporter bioassay (Promega) with A/Wisconsin/67/200 (H3N2)-overexpressing 3T3 cells was initially used to test the ability of the H1H14611N2 and H1H14612N2 antibodies to specifically lyse HA-decorated cells. Target cells were combined with the indicated mAbs at the indicated concentrations. Target and effector cells were then combined at an E:T ratio of 5:1. Shown in FIG. 3 are the results of this assay using H1H14611N2 (triangles), H1H14612N2 (inverse triangles), along with an irrelevant hIgG1 (diamonds) as a control.

B. ADCC Assay Using Human Donor Peripheral Blood Mononuclear Cells (PBMCs)

Figure 4:
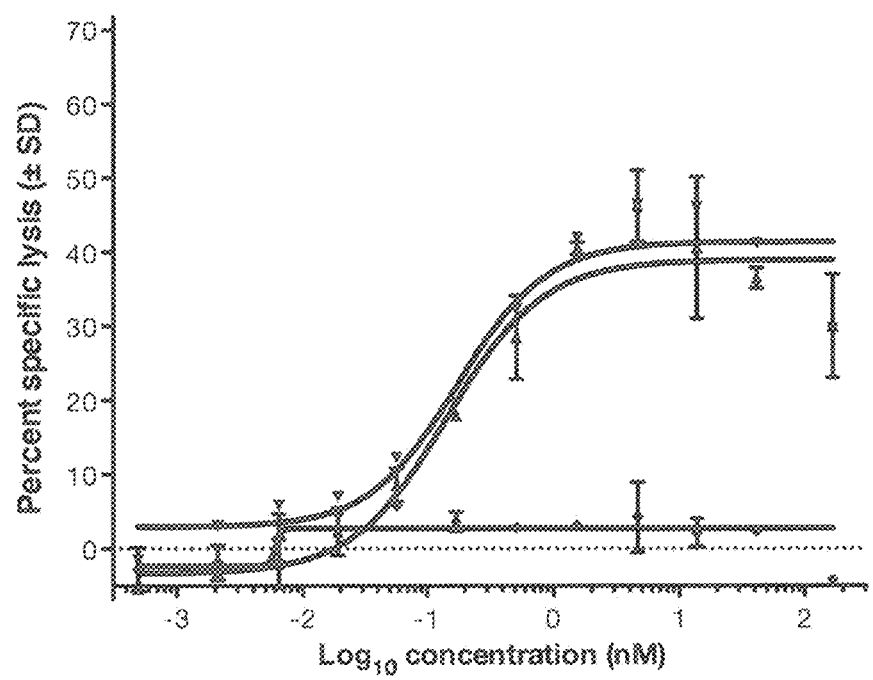
FIG. 4: Shows a dose response curve of anti-group 2 HA antibodies H1H14611N2 and H1H14612N2 in an ADCC assay using human donor PBMCs.

The two exemplary anti-group 2 HA antibodies, H1H14611N2 and H1H14612N2, were then tested in an ADCC assay using human donor PBMCs. PBMCs were isolated from human donor buffy coats and stimulated with IL-2 (5 ng/mL) for 10 to 12 h prior to use. A/Wisconsin/67/2005 (H3N2)-overexpressing 3T3 target cells were combined with the indicated mAbs at the indicated concentrations. Target and effector cells were then combined at an E:T ratio of 30:1. Percent cytotoxicity was measured using CytoTox-Glo (Promega). Shown in FIG. 4 are the results of this assay using H1H14611N2 (circles), H1H14612N2 (inverse triangles), along with an irrelevant hIgG1 (diamonds) as a control.

Results

H1H14611N2 and H1H14612N2 displayed a dose-dependent increase in ability to specifically lyse HA-decorated cells in both ADCC assays.

H1H14611N2 and H1H14612N2 showed a dose-dependent increase in FcγRIIIA activation in the ADCC-Glo reporter bioassay (Promega) with A/Wisconsin/67/2005 (H3N2)-overexpressing 3T3 cells (FIG. 3). The $EC_{50}$ for H1H14611N2 was 0.8714 nM and for H1H14612N2 was 0.6882 nM.

ADCC activity was confirmed using direct PBMC-mediated cytotoxicity of infected and overexpressing cells. Using human donor PBMCs, H1H14611N2 and H1H14612N2 mediated ADCC on A/Wisconsin/67/2005 (H3N2)-overexpressing 3T3 cells (FIG. 4). The $EC_{50}$ for H1H14611N2 was 0.1463 nM and for H1H14612N2 was 0.1762 nM.

An effector to target (E:T) ratio of 30:1 was used for all experiments using donor PBMCs, while an E:T of 5:1 was used for the reporter bioassay.

Example 7: Selected Group 2-Specific Influenza a Hemagglutinin Monoclonal Antibodies Effectively Treat Lethal Influenza Virus Infection In Vivo There is a substantial unmet need for improved standard of care therapies for treating or preventing of influenza virus infections in humans. Currently, only two classes of drugs are available: the adamantanes and the neuraminidase inhibitors (NAIs). Adamantanes (amantadine and rimantadine) have been associated with the rapid emergence of drug-resistant strains and are no longer recommended for treatment of influenza. NAIs like oseltamivir (TAMIFLU®) are the front line drugs for treatment and prophylaxis of influenza, however, their window of efficacy is limited: NAIs have been shown to reduce the duration of fever and illness symptoms by about one day in the therapeutic setting if the antiviral is administered within 48 hours of symptom onset with little clinical evidence for efficacy if administered after 48 hours.

To evaluate the in vivo efficacy of H1H14611N2 and H1H14612N2 in the treatment of severe influenza, experiments were conducted with the following objectives:

Study 1: To evaluate the efficacy of a single dose of H1H14611N2 and H1H14612N2.

Study 2: To determine the efficacy of H1H14611N2 administered in combination with oseltamivir.

The strain used in these studies was a mouse-adapted A/Aichi/02/1968-X31 (H3N2) influenza A virus group 2 isolate. All experiments were performed in 6-week-old wild-type (BALB/c) female mice. Mice were challenged with $5 \times MLD_{50}$ (10,000 PFUs) of A/Aichi/02/1968-X31 (H3N2). In the treatment models, mice were challenged intranasally (IN) on day 0 and fixed IV doses of mAb were given on a specific day post infection (p.i.). Oseltamivir was resuspended according to the manufacturers instructions and mice were dosed every 12 h (i.e., twice per day, BID) via oral gavage for 5 days with the first dose administered on day 4. Mice were weighed and observed daily up to day 14 p.i. and were sacrificed when they lost 20% of their starting weight. Results are reported as percent survival.

Figure 5A:
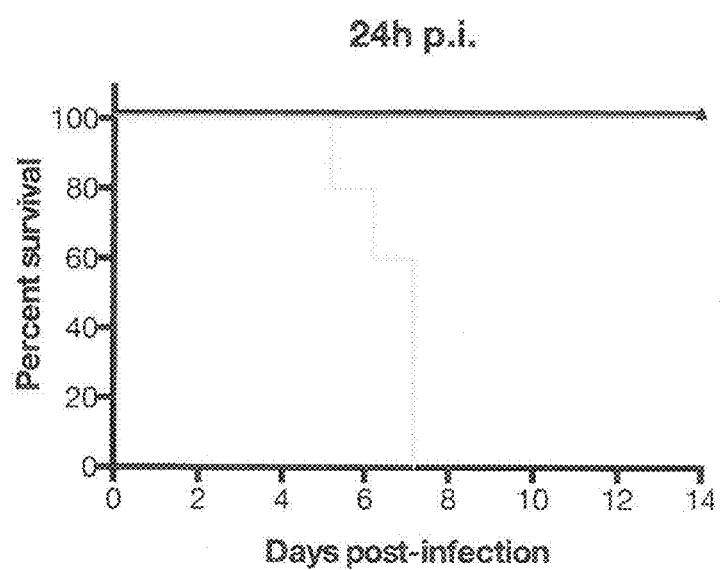

In the first experiment we compared the efficacy of either a single dose of H1H14611N2 (15 mg/kg; triangles) or H1H14612N2 (15 mg/kg; inverse triangles) initiating 24, 48 or 72 hours post-infection with $5 \times MLD_{50}$ of A/Aichi/02/1968-X31 (H3N2) to evaluate the effect in the murine model at these timepoints. All mice receiving 15 mg/kg of an isotype control at 24 hours post-infection died by day 7 (shown in FIG. 5A only as a solid gray line); in contrast, all mice receiving a single dose (15 mg/kg) of H1H14611N2 or H1H14612N2 survived when dosed at 24 (FIG. 5A), 48 (FIG. 5B), or even 72 (FIG. 5C) hours post-infection.

Figure 6:
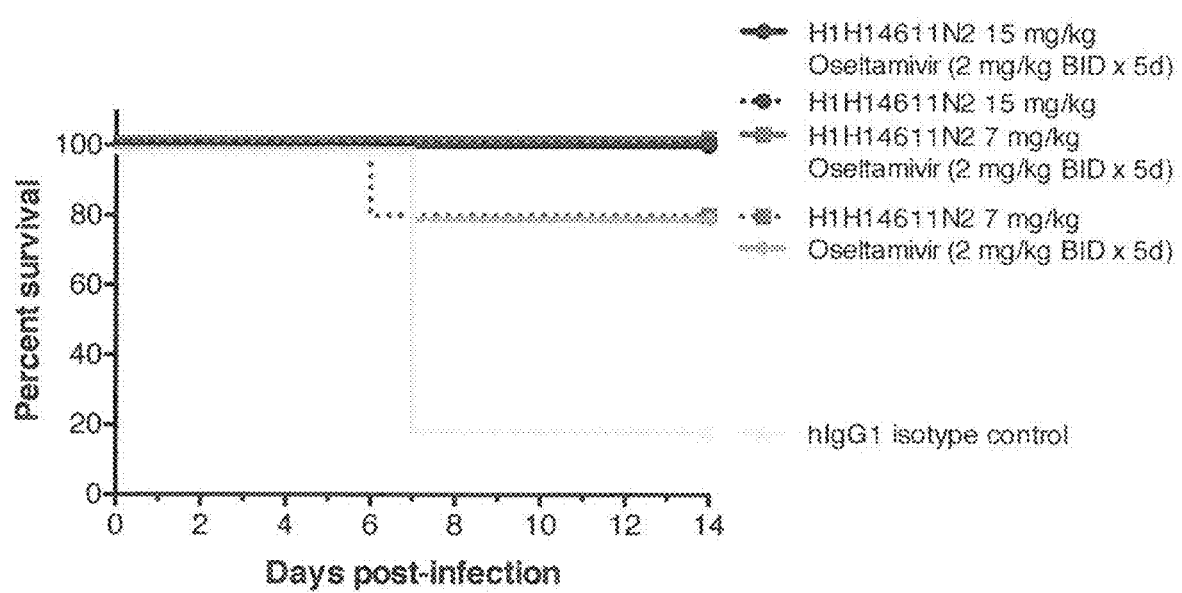
FIG. 6: Shows that anti-group 2 HA antibody H1H14611N2 has an additive effect on the treatment of influenza infection when dosed in combination with oseltamivir 96 hours after infection.

In the second experiment, mice received a single sub-efficacious dose of 7 mg/kg (squares, dotted line) or 15 mg/kg of H1H14611N2 (circles, dotted line), control IgG (triangles), 2 mg/kg BID oseltamivir for 5 days (diamonds, solid line) or a combination of a single dose of 7 (squares, solid line) or 15 mg/kg H1H14611N2 (circles, solid line) and oseltamivir for 5 days 96 hours after infection with $5 \times MLD_{50}$ of A/Aichi/02/1968-X31 (H3N2) (See FIG. 6). Single doses of H1H14611N2 at 15 mg/kg and 7 mg/kg resulted in 100% and 80% survival, respectively, and 80% of mice treated with 2 mg/kg oseltamivir alone survived. Combining H1H14611N2 with oseltamivir increased survival to 100% in both H1H14611N2 dose groups (15 mg/kg or 7 mg/kg) demonstrating that the combination allows lower doses of H1H14611N2 to achieve a robust treatment effect (FIG. 6).

To summarize, H1H14611N2 and H1H14612N2 displayed robust efficacy in treating mice infected with a historical influenza strain, and furthermore H1H14611N2 showed additive efficacy when administered in combination with oseltamivir.

What is claimed is:

1. An isolated recombinant antibody or antigen-binding fragment thereof that specifically binds to group 2 influenza A hemagglutinin (HA), wherein the antibody or fragment thereof comprises:
   (a) three heavy chain complementarity determining regions (CDRs) (HCDR1, HCDR2, and HCDR3) contained within a heavy chain variable region (HCVR) comprising the amino acid sequence set forth in SEQ ID NO: 2; and three light chain CDRs (LCDR1, LCDR2, and LCDR3) contained within a light chain variable region (LCVR) comprising the amino acid sequence set forth in SEQ ID NO: 10; or
   (b) three heavy chain CDRs (HCDR1, HCDR2, and HCDR3) contained within an HCVR comprising the amino acid sequence set forth in SEQ ID NO: 18; and three light chain CDRs (LCDR1, LCDR2, and LCDR3) contained within an LCVR comprising the amino acid sequence set forth in SEQ ID NO: 26.

2. The isolated antibody of claim 1, wherein, when administered to an influenza virus infected mammal as a single intravenous dose of about 7 to 15 mg/kg starting at day 3 post-infection, protects the mammal from said infection to a greater degree than that of an influenza virus infected mammal that has received oral administration of oseltamivir administered twice daily for 5 days at a dose of about 2 mg/kg starting at day 3 post-infection and continuing until day 7 post-infection.

3. The isolated antibody of claim 1, wherein, when administered as a single dose of about 15 mg/kg at 96 hours post-infection, to mammals infected with influenza virus, said mammals have a survival rate of about 100%.

4. The isolated antibody of claim 1, wherein when administered as a single dose of about 15 mg/kg to mammals infected with influenza virus, said mammals have a survival rate of about 100%.

5. The isolated antibody of claim 1, wherein, when administered to a mammal infected with influenza virus, demonstrates an additive protective effect in the mammal when administered with oseltamivir at 96 hours post-infection.

6. The isolated antibody of claim 1, wherein, when administered to a mammal infected with influenza virus as a single intravenous dose ranging from about 7 mg/kg to about 15 mg/kg, demonstrates an additive protective effect in the mammal when administered in combination with oseltamivir orally twice daily for 5 days at a dose of about 2 mg/kg.

7. The isolated antibody or antigen-binding fragment thereof of claim 1, comprising an HCVR having an amino acid sequence as set forth in SEQ ID NO: 2 and an LCVR having an amino acid sequence as set forth in SEQ ID NO: 10.

8. The isolated antibody or antigen-binding fragment thereof of claim 1, comprising an HCVR having an amino acid sequence as set forth in SEQ ID NO: 18 and an LCVR having an amino acid sequence as set forth in SEQ ID NO: 26.

9. The isolated antibody or antigen-binding fragment thereof of claim 1, comprising wherein the antibody has one or more of the following characteristics:
(a) is a fully human monoclonal antibody;
(b) binds to influenza A group 2 HA with a dissociation constant ($K_D$) of less than $10^{-8}$ M, as measured by surface plasmon resonance;
(c) demonstrates a dissociative half-life ($t_{1/2}$) greater than 75 minutes;
(d) demonstrates neutralization of influenza A group 2 viruses selected from H3N2 and H7N9 strains with an IC50 of less than 200 nM and 500 nM, respectively;
(e) demonstrates complement mediated lysis of influenza virus infected cells with an EC50 of less than about 150 nM;
(f) demonstrates antibody-dependent cell-mediated cytotoxicity of virus infected target cells using a reporter bioassay with an EC50 of less than about 0.9 nM;
(g) demonstrates antibody-dependent cell-mediated cytotoxicity of virus infected target cells in the presence of human peripheral blood mononuclear cells (PBMC) with an EC50 of less than about 0.180 nM;
(h) demonstrates an increase in survival in an influenza-infected animal when administered at 24, 48, 72, or 96 hours after virus challenge; or
(i) demonstrates an increase in survival in an influenza-infected animal when administered in combination with oseltamivir at 96 hours after infection.

10. The isolated antibody or antigen-binding fragment thereof of claim 1, comprising:
(a) a HCDR1 of SEQ ID NO: 4,
(b) a HCDR2 of SEQ ID NO: 6;
(c) a HCDR3 of SEQ ID NO: 8;
(d) a LCDR1 of SEQ ID NO: 12;
(e) a LCDR2 of SEQ ID NO: 14; and
(f) a LCDR3 of SEQ ID NO: 16.

11. The isolated antibody or antigen-binding fragment thereof of claim 1, comprising:
(a) a HCDR1 of SEQ ID NO: 20,
(b) a HCDR2 of SEQ ID NO: 22;
(c) a HCDR3 of SEQ ID NO: 24;
(d) a LCDR1 of SEQ ID NO: 28;
(e) a LCDR2 of SEQ ID NO: 30; and
(f) a LCDR3 of SEQ ID NO: 32.

12. The isolated antibody of claim 1, wherein the antibody blocks attachment to and/or entry of influenza virus into a host cell.

13. A pharmaceutical composition comprising an isolated antibody or antigen-binding fragment thereof that binds to influenza HA according to claim 1 and a pharmaceutically acceptable carrier or diluent.

14. An isolated polynucleotide molecule comprising a polynucleotide sequence that encodes a HCVR or an LCVR of an antibody as set forth in claim 1.

15. A vector comprising the polynucleotide of claim 14.

16. A cell expressing the vector of claim 15.

17. A method of treating or ameliorating at least one symptom of influenza infection in a subject in need thereof, the method comprising administering an antibody or antigen-binding fragment of claim 1, or a pharmaceutical composition comprising said antibody or antigen-binding fragment thereof to the subject in need thereof.

18. The method of claim 17, wherein the at least one symptom is selected from the group consisting of fever, cough, body aches, rhinorrhea, shortness of breath, pneumonia and bronchitis.

19. The method of claim 17, wherein the pharmaceutical composition is administered to a subject selected from the group consisting of an immunocompromised individual, an elderly adult (more than 65 years of age), a healthcare worker, and a person with a history of medical problems or an underlying medical condition.

20. The method of claim 17, wherein the pharmaceutical composition is administered in combination with a second therapeutic agent.

21. The method of claim 20, wherein the second therapeutic agent is selected from the group consisting of an anti-viral drug, an anti-inflammatory drug, a different antibody that binds specifically to influenza HA from group 1 or group 2, a vaccine for influenza, a dietary supplement and any other palliative therapy to treat an influenza infection.

22. The method of claim 21, wherein the second therapeutic agent is administered via a different route of administration as the antibody or antigen-binding fragment thereof.

23. The method of claim 22, wherein the second therapeutic agent is administered orally.

24. The method of claim 21, wherein the anti-viral drug is oseltamivir.

25. The method of claim 24, wherein the oseltamivir is administered prior to, concurrently with, or after administration of the antibody.

26. The method of claim 17, wherein the pharmaceutical composition is administered subcutaneously, intravenously, intradermally, intramuscularly, intranasally, or orally.

* * * * *